(12) United States Patent
Diamant et al.

(10) Patent No.: US 9,526,646 B2
(45) Date of Patent: Dec. 27, 2016

(54) STENT REPLACEMENT SYSTEM

(75) Inventors: Valery Diamant, Katzrin (IL);
Nadezda Yasko, Tomsk (RU); Boris Varshitsky, Jerusalem (IL); Nachum Borivker, Jerusalem (IL); Chaim Lotan, Jerusalem (IL)

(73) Assignee: MEDKARDIA LTD., Katsrin (IL)

( * ) Notice: Subject to any disclaimer, the term of this patent is extended or adjusted under 35 U.S.C. 154(b) by 376 days.

(21) Appl. No.: 12/745,617

(22) PCT Filed: Dec. 3, 2008

(86) PCT No.: PCT/IL2008/001573
§ 371 (c)(1),
(2), (4) Date: Jun. 1, 2010

(87) PCT Pub. No.: WO2009/072122
PCT Pub. Date: Jun. 11, 2009

(65) Prior Publication Data
US 2010/0305679 A1  Dec. 2, 2010

Related U.S. Application Data

(60) Provisional application No. 60/991,927, filed on Dec. 3, 2007.

(51) Int. Cl.
*A61F 2/82* (2013.01)
*A61F 2/958* (2013.01)
*A61F 2/954* (2013.01)

(52) U.S. Cl.
CPC ............. *A61F 2/958* (2013.01); *A61F 2/954* (2013.01); *A61F 2002/821* (2013.01)

(58) Field of Classification Search
CPC ...... A61F 2/954; A61F 2/958; A61F 2002/821
(Continued)

(56) References Cited

U.S. PATENT DOCUMENTS 5,104,399 A * 4/1992 Lazarus ............... 623/1.14
5,749,890 A   5/1998 Shaknovich
(Continued)

FOREIGN PATENT DOCUMENTS

| EP | 1844738 A1 | 10/2007 | |
| WO | WO2006127825 A * | 11/2006 | ............... A61F 2/06 |
| WO | WO2006127825 A1 | 11/2006 | |

*Primary Examiner* — Diane Yabut
(74) *Attorney, Agent, or Firm* — Brondy and Neimark, PLLC

(57) ABSTRACT

A system for delivering and placement of a medical prosthesis into an ostium of a tract system of an organism is described. The system comprises a stent delivery device that includes a delivery catheter having one or more lumens extending between proximal and distal ends. The stent delivery device also includes an inflatable balloon mounted on the distal end of the delivery catheter for expanding and deploying the medical prosthesis placed on the balloon, and a stent deployment site locator configured for locating an exact place for positioning the medical prosthesis. The deployment site locator comprises an expandable flexible structure including a plurality of filament elements interconnected between a locator proximal end and a locator distal end; thereby forming a unitary structure. The filaments can extend from a locator proximal end towards a locator distal end and then return after winding to the proximal end to form a plurality of filament loops.

21 Claims, 21 Drawing Sheets

(58) Field of Classification Search
USPC .......................................................... 623/1.11
See application file for complete search history.

(56) References Cited

U.S. PATENT DOCUMENTS

| | | |
|---|---|---|
| 7,410,482 B2 * | 8/2008 | Murphy et al. .................... 606/1 |
| 2003/0171739 A1 * | 9/2003 | Murphy et al. .................... 606/1 |
| 2004/0116946 A1 | 6/2004 | Goldsteen |
| 2004/0181272 A1 | 9/2004 | Chambers |
| 2007/0021819 A1 * | 1/2007 | Krolik et al. ................. 623/1.11 |
| 2007/0156221 A1 | 7/2007 | Varshitzky |
| 2007/0173918 A1 | 7/2007 | Dreher |
| 2007/0239252 A1 * | 10/2007 | Hopkins et al. ............. 623/1.11 |
| 2008/0086149 A1 * | 4/2008 | Diamant et al. .............. 606/113 |

* cited by examiner

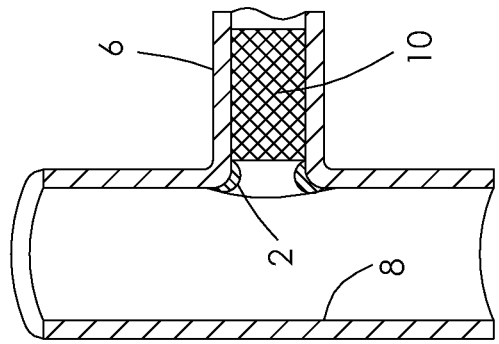
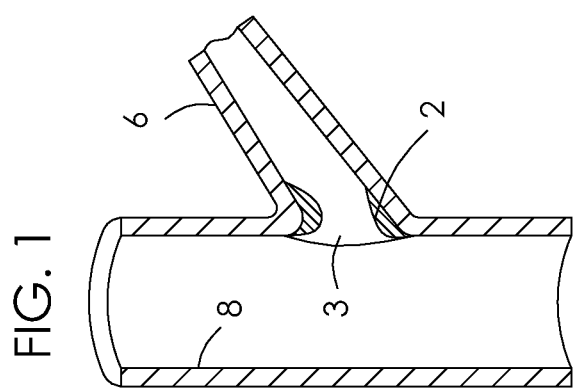
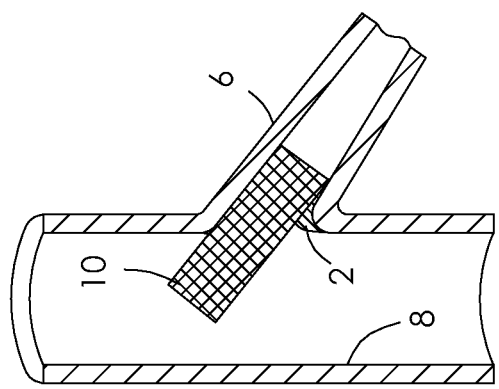

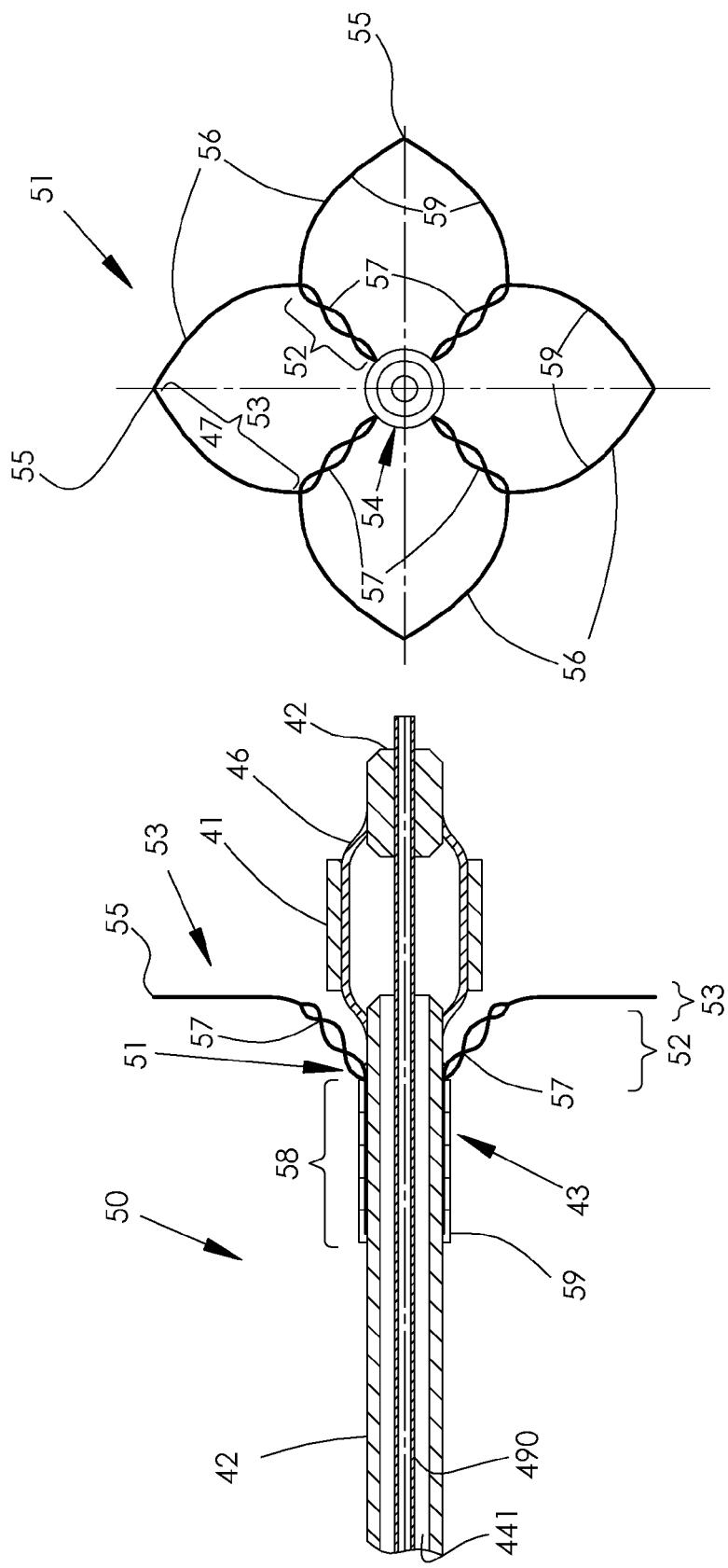

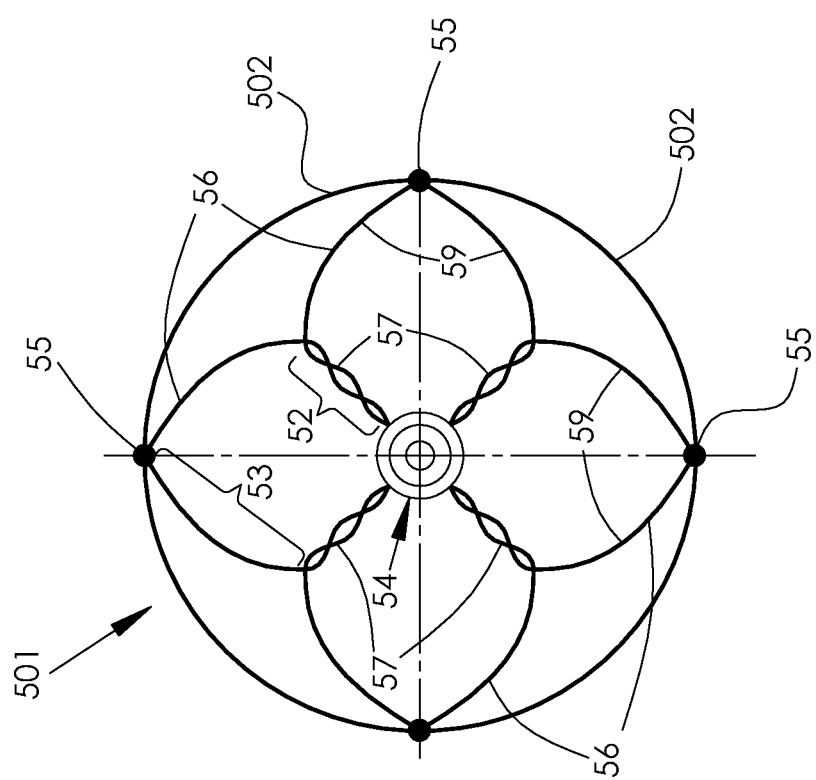

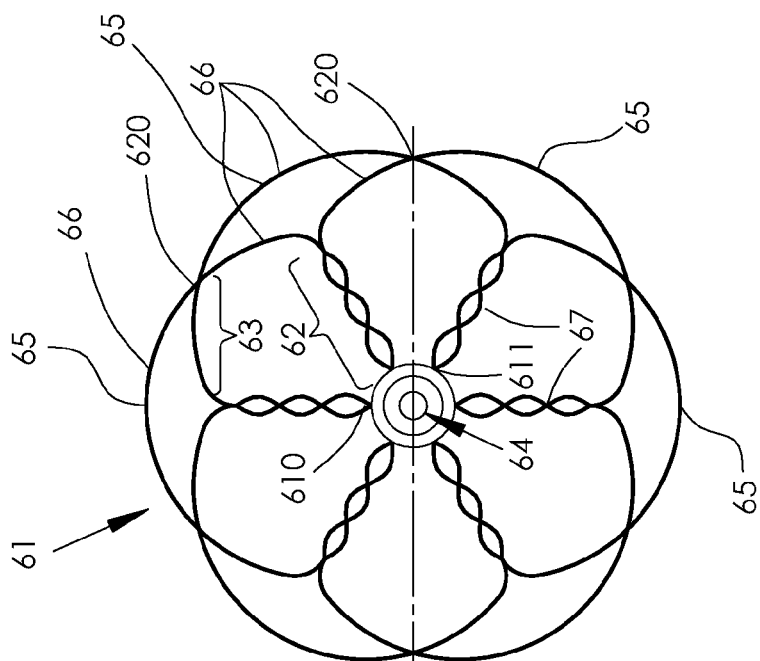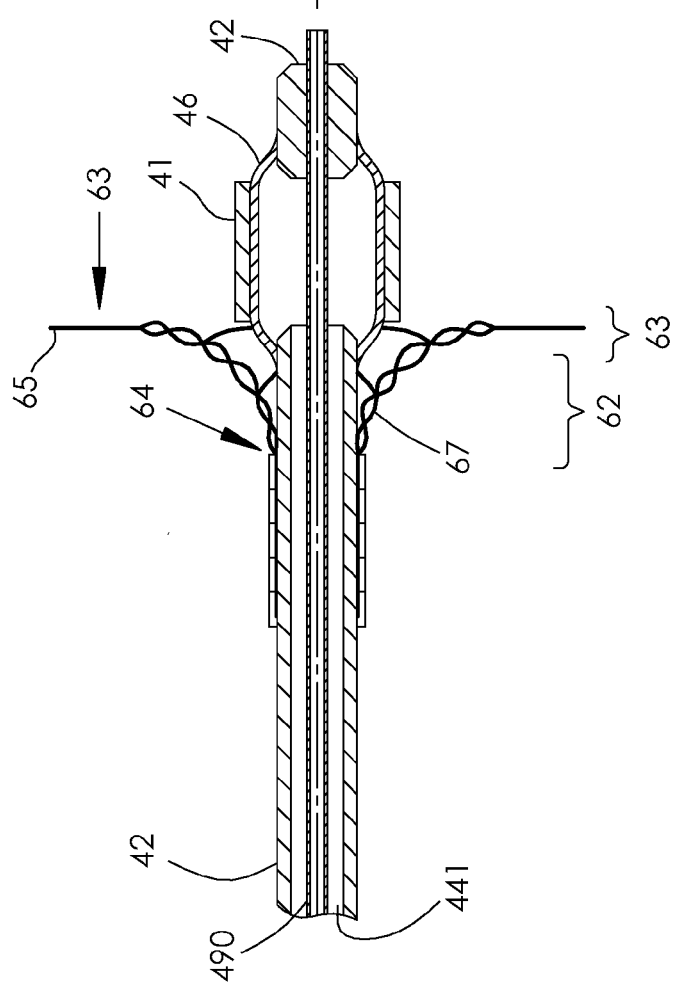
FIG. 6B
FIG. 6A

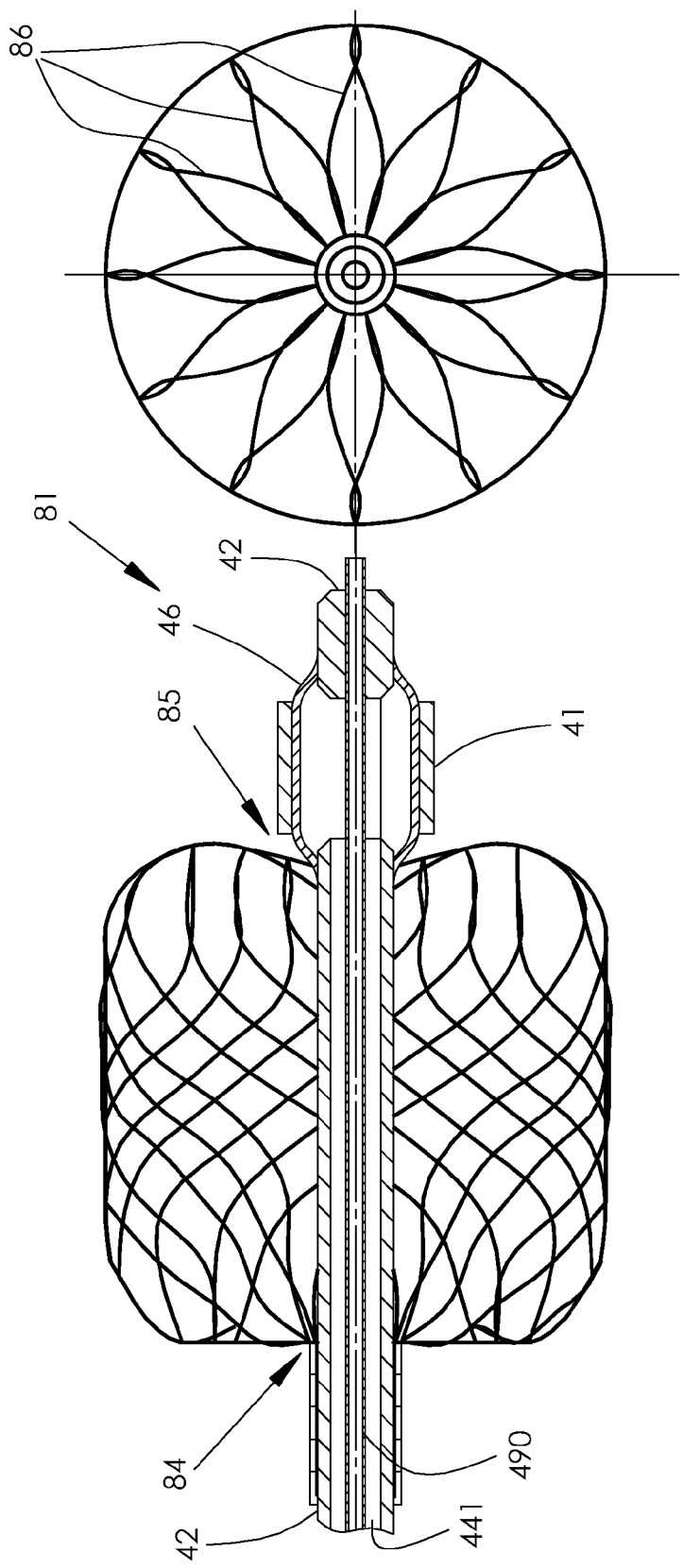

STENT REPLACEMENT SYSTEM

RELATED APPLICATIONS

This application is a Continuation of International Application No. PCT/IL2008/001573 filed on Dec. 3, 2008, which claims priority to U.S. Provisional Patent Application No. 60/991,927 filed on Dec. 3, 2007, both of which are incorporated herein by reference in their entirety.

FIELD OF THE INVENTION

This invention relates generally to a system and method for locating an ostium of a blood vessel, and, more specifically, to a stent delivery and placement system.

BACKGROUND OF THE INVENTION

Lesions in blood vessels can result from a build-up of an atherosclerotic plaque. The plaque build-up causes a narrowing of the vessel and reduced blood flow therein. In the case of lesions in coronary arteries such reduced blood flow can lead to heart disease and death.

Atherosclerotic lesions can also occur at or near an ostium—the opening of a branching conduit. Ostial lesions damage the ostium of a branching conduit. In aorto-ostial lesions, the treatment outcome using conventional balloon angioplasty has been limited by a low success rate and high incidence of restenosis, or recurrence of artery blockage. An attractive alternative for the treatment of this subset of lesions is coronary stenting.

Coronary stent therapy of aorto-ostial lesions is limited by the need to precisely position the intravascular stent completely within the vascular lumen and as close as possible to the ostium. Limited visualization of the coronary artery ostium, angulations of the aorto-coronary segment and difficulties in the placement of the guiding catheter are all factors that affect the final result. If the stent is not placed far enough into the branch vessel, it extends into the aorta and thus may be subject to trauma from the guiding catheter. In this case, stent protrusion into the aortic lumen interferes with aortic blood flow and hastens further aortic catheterization. On the other hand, if the stent is placed too far into the branch vessel, it may miss the ostium and the tightest portion of the stenosis. In addition, there is the potential to compromise the lumen and subject the patient to a higher incidence of sub-acute stent thrombosis or restenosis, as well as a high risk for dissection, acute closure or rupture.

Various stent placement systems for delivering stents to a vascular lumen immediately adjacent to an ostium are well known in the art. Such systems can utilize a balloon which is inflated around the catheter and used as a positioner against the ostial opening.

For example, U.S. Pat. No. 5,749,890 describes a stent delivery assembly and method for stent placement in an ostial lesion. In particular, the stent delivery system of the invention comprises a break segment which changes configuration to facilitate localization of the target ostium.

Balloon locators can function as a unitary body, however, since such balloons form a fairly rigid structure when inflated, angulation of an attached catheter with respect to an ostium while maintaining full contact between the balloon and the ostial opening, can be difficult if not impossible with such systems. Use of inflatable balloons is also limited by the need for complex inflation mechanisms.

Locators are also known which include individual wire or polymer struts which are extended around the catheter and function as individual stops, each contacting a region of the ostial opening.

For example, U.S. Pat. Appl. Publication No. 2004/181272A1 describes a stent combined with a positioning apparatus to effectively place the stent at a precise deployment site within a narrowed vascular region such as an artery. The stent is maneuvered through the vessel and is guided by a guiding catheter up the vessel to where the narrowing is located. Upon exiting the guiding catheter and approaching the deployment site within the coronary artery, a deployment site locator expands to contact the vascular structure and, thereby, effectively position the stent at the deployment site within the narrowed vessel.

U.S. Pat. Appl. Publication No. 2007/156221A1 describes a stent positioning system, including an inflatable balloon for expanding a stent. The balloon, in its collapsed state, fits into and is adapted to carry the stent in its pre-expanded condition. Stent locator means are slidably accommodated in a guide catheter and adapted to change its shape prior to making contact with the interior wall surface of a major blood vessel in the ostial region of a smaller blood vessel branching off from the major vessel and prior to the expansion of the stent. Mechanical means for changing the shape of the stent locator means are also provided. The change of shape enables the locator means to abut the interior wall surface, thereby ensuring correct apposition between the stent and the ostium of the smaller blood vessel.

Locators in the form of independent and not interconnected loops are also known. For example, U.S. Pat. Appl. Publication No. 2007/173918A1 describes an apparatus and method for locating an ostium of a branch vessel. The apparatus includes a delivery catheter having a distal end sized for introduction into the branch, and locator elements including first ends fixed to the distal end and second ends free from the distal ends. The locator elements can be in the form of loops which are compressible from a transverse, deployed condition to an axial, contracted condition, wherein the second ends are disposed proximal to the first ends. During use, the catheter is directed through a guide catheter into the ostium with the locator elements compressed, and the locator elements are deployed within the branch in the contracted condition. The catheter is partially withdrawn from the branch, the locator elements resiliently expanding towards the deployed condition as they enter the main vessel. The catheter may be used to deliver a stent into the branch with the expanded locator elements facilitating positioning the stent.

Locators with individual strut and loop attempt to overcome the limitations of balloon locators by providing independently movable struts and loops which are mechanically deployed and maintain independent contact with the tissue surrounding the ostium during catheter angulation. Although such configurations can in theory provide better catheter maneuverability, use of individual struts and loops can lead to strut mis-positioning and as a result escape of an individual strut(s) and/or loop(s) into the branch vessel.

SUMMARY OF THE INVENTION

There is a need in the art to provide a stent delivery system that prevents both too distal and too proximal placement and implantation of the stent, i.e., a system that ensures proper stent-to-vessel positioning.

It would also be advantageous to have a locator device which includes expandable locator elements that are elastically compliant while maintaining a single unitary structure.

It would also be advantageous to have a locator device which includes expandable locator elements that forms a flexible, elastically compliant unitary structure when expanded.

The present invention provides a comprehensive approach for accurate stent positioning. Generally, this approach provides a stent delivery system including one or more novel stent deployment site locators, attached to a guide catheter for a typical inflatable balloon outfitted stent.

The present invention satisfies the aforementioned need by providing a novel system for delivering and placement of a stent or other medical prosthesis into or near an ostium of a vascular system or other tract system of an organism.

As used herein, the phrase "medical prosthesis" refers to any device which can be delivered into the body, specifically to a vessel such as a blood vessel. Examples of medical devices include, but are not limited to, stents, probes, angioplasty balloons and the like.

The system comprises a delivery catheter having a proximal end, a distal end, and at least one lumen extending between the proximal and distal ends. The delivery catheter also includes an inflatable balloon mounted on the distal end of the delivery catheter for expanding and deploying the medical prosthesis placed on the balloon, and a stent deployment site locator configured for locating an exact place for positioning and facilitating the positioning of the medical prosthesis in or near an ostium.

The deployment site locator comprises a plurality of filament elements that are interconnected between a locator proximal end and a locator distal end; thereby forming a unitary structure. The filament elements can be maintained in a compacted state within or on a catheter and expanded to form an interconnecting, interlocking or overlapping unitary structure. The deployment site locator maintains a unitary and flexible structure (when expanded) and capable of being angled with respect to a longitudinal axis of a delivery catheter coupled to the locator.

According to one embodiment of the present invention, the filament elements of the deployment site locator extend from a locator proximal end towards a locator distal end and then return after winding to the proximal end to form a plurality of filament loops. Contrary to the individual struts and loops of the prior art, the deployment site locator of the present invention includes interlocked or overlapping filament loops.

The deployment site locator of the present invention can be integrated into a dedicated catheter system or configured as an add-on device which is attachable to standard or modified stent delivery catheter systems.

According to one embodiment of the present invention, the stent deployment site locator is mounted on the delivery catheter at the distal end before the inflatable balloon in relation to an operator using the system.

According to another embodiment of the present invention, the stent deployment site locator is mounted on the delivery catheter at the distal end after the inflatable balloon in relation to an operator using the system.

According to one embodiment of the present invention, the system for delivering and placement of a medical prosthesis comprises a carrier catheter configured for carrying the stent deployment site locator. The carrier catheter has a proximal end, a distal end, and an axially extending inner lumen provided within the carrier catheter to permit the stent delivery device to be inserted into the carrier catheter from the proximal end. The stent deployment site locator is mounted on the carrier catheter at the distal end.

According to yet another embodiment of the present invention, the system for delivering and placement of a medical prosthesis comprises a clamp arranged on the carrier catheter for binding or pressing the carrier catheter and the delivery catheter together so as to hold them firmly and prevent their relative motion with respect to each other.

According to still another embodiment of the present invention, the system for delivering and placement of a medical prosthesis comprises a guiding catheter including a lumen for housing the delivery catheter. The lumen has sufficient size for receiving the distal end of the delivery catheter therethrough together with the stent deployment site locator in a contracted condition.

According to a further embodiment of the present invention, the system for delivering and placement of a medical prosthesis comprises a guiding catheter including a lumen for housing the carrier catheter. The lumen has sufficient size for receiving the distal end of the carrier catheter therethrough together with the stent deployment site locator in a contracted condition.

According to one embodiment of the present invention, an outer diameter of the carrier catheter is less than an inner diameter of the guiding catheter to permit the carrier catheter to move within the guiding catheter.

According to a further embodiment of the present invention, the system for delivering and placement of a medical prosthesis comprises a manipulator configured for manipulating the stent placement system for delivering and placing the medical prosthesis.

According to one embodiment of the present invention, each filament of the plurality of filament elements originates from a certain point at the locator proximal end, and extends towards the locator distal end to form a loop and then returns to the same point at the locator proximal end.

According to one embodiment of the present invention, the loops of the plurality of filament loops are not interconnected at said locator distal end.

According to another embodiment of the present invention, a distal end of each loop is coupled to a distal end of the neighboring loops by means of a reinforcement wire to provide mechanical strengthening to the stent deployment site locator.

According to still another embodiment of the present invention, each loop is overlapped and/or interlaced with at least one other neighboring loop.

According to yet another embodiment of the present invention, the loops are directly bound to each other at overlapped points of the neighboring loops to provide mechanical strengthening to the stent deployment site locator.

According to still a further embodiment of the present invention, at least one wire is twisted around the loops at their distal ends.

According to one embodiment of the present invention, each side of each loop is directly connected to a side of an adjacent loop at more than one point, thereby to provide structural rigidity and dilatation ability to said deployment site locator.

According to another embodiment of the present invention, the connection of the sides of the loops along said proximal portion is achieved by twisting each pair of the filaments forming the corresponding sides.

According to yet another embodiment of the present invention, the filaments of the plurality filament elements are made of metallic material having superelastic and thermo-mechanical shape memory characteristics. For example, the metallic material includes a radiopaque material.

According to still another embodiment of the present invention, the filaments are made of non-metallic material.

According to one embodiment of the present invention the system for delivering and placement of a medical prosthesis comprises a guide wire extending from a guide wire port at the proximal end of the stent delivery device through the lumen of the delivery catheter to an opening arranged in a tip of the distal end of the delivery catheter.

For example, the guide wire port is arranged at the proximal end of the delivery catheter.

According to another example, the guide wire port is arranged in a wall of the delivery catheter.

According to yet another example, the guide wire port is arranged in a wall of the carrier catheter.

According to still another example, the guide wire is fixed at the distal end of the delivery catheter.

There has thus been outlined, rather broadly, the more important features of the invention in order that the detailed description thereof that follows hereinafter may be better understood. Additional details and advantages of the invention will be set forth in the detailed description, and in part will be appreciated from the description, or may be learned by practice of the invention.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 1 shows a typical aorto-ostial lesion;

FIGS. 2 and 3 illustrate two types of faulty prior art stent-to-vessel apposition;

FIG. 5A and FIG. 5B illustrate side and top views of the distal portion of the delivery device of FIG. 4A equipped with a stent deployment site locator, respectively, according to one embodiment of the present invention;

FIG. 5C illustrates a top view of the distal portion of the delivery device of FIG. 4A equipped with a stent deployment site locator, according to one embodiment of the present invention;

FIG. 6A and FIG. 6B illustrate side and top views of the distal portion of the stent delivery device equipped with a stent deployment site locator, respectively, according to another embodiment of the present invention;

FIG. 8A and FIG. 8B illustrate side and top views of the distal portion of the stent delivery device equipped with a stent deployment site locator, according to still another embodiment of the present invention;

DETAILED DESCRIPTION OF EMBODIMENTS

Figure 4A:
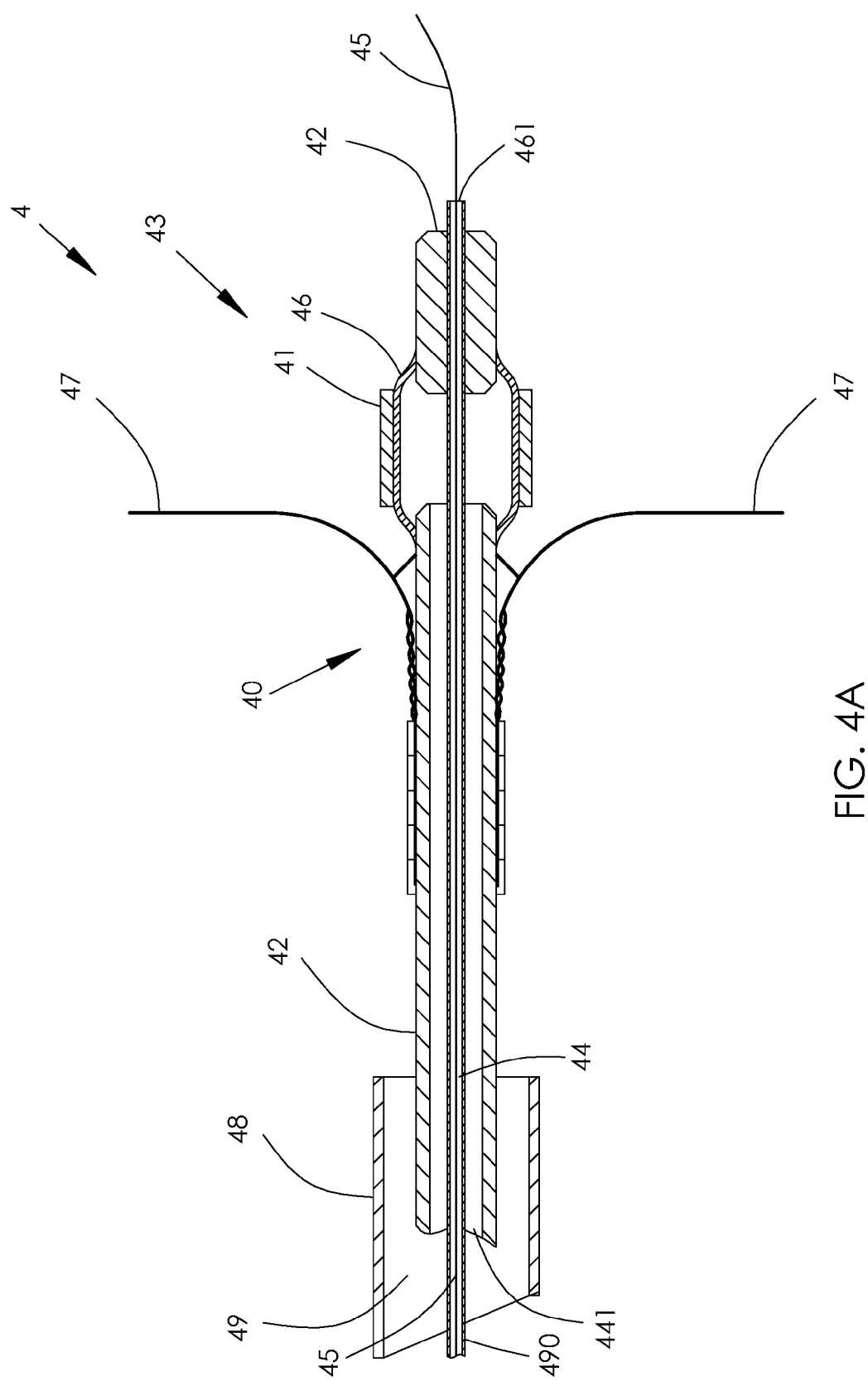
FIG. 4A illustrates a schematic longitudinal top cross-sectional fragmentary view of a distal portion of a stent placement system, according to one embodiment of the present invention.

The principles of the medical device according to the present invention may be better understood with reference to the drawings and the accompanying description, wherein like reference numerals have been used throughout to designate identical elements. It being understood that these drawings which are not necessarily to scale, are given for illustrative purposes only and are not intended to limit the scope of the invention. Examples of constructions, materials, dimensions, and manufacturing processes are provided for selected elements. Those versed in the art should appreciate that many of the examples provided have suitable alternatives which may be utilized. As used throughout this description, proximal and distal orientation relationships are in relation to an operator (e.g., surgeon) utilizing the invention as described herein.

Referring now to the drawings, FIG. 1 illustrates a typical ostial lesion, defined as a lesion arising within several millimeters of the origin of the blood vessel. More specifically, FIG. 1 illustrates an aorto-ostial atherosclerotic lesion that produces a significant stenosis 2 at the ostium 3 of a coronary artery 6, where the artery branches off the aorta 8.

FIGS. 2 and 3 illustrate faulty prior art stent-to-vessel apposition. In FIG. 2, a stent 10 is implanted in too proximal location and is seen to project into an aorta 8, where it is subject to trauma from the guiding catheter and is also liable to compromise the lumen of the aorta, increasing the danger of stent thrombosis and re-stenosis. In FIG. 3, the stent 10 is placed in too distal a location, missing the ostium 2 and the tightest portion of the stenosis.

Referring to FIG. 4A, a schematic longitudinal cross-sectional fragmentary view of a distal portion of a stent placement system 4 for delivering and placement of a stent or other desired medical prosthesis 41 into an ostium or other bifurcation of a vascular system or other tract of an organism (not shown) is illustrated, according to one embodiment of the present invention. It should be understood that the system 4 is not bound to the scale and proportion illustrated in FIG. 4A and in other drawings.

Generally, the stent placement system 4 includes a stent delivery device 40, a guiding catheter 48 and a manipulator (not shown in FIG. 4A) configured for manipulating the stent placement system 4 for delivering and placing the stent 41.

The stent delivery device 40 includes a delivery catheter 42 that is in the form of an elongate tubular member having a proximal end (not shown), a distal end 43, and one or more lumens 44 extending between the proximal and distal ends, thereby defining a longitudinal axis (not shown) between the proximal and distal ends. The delivery catheter 42 is a deflectable tube fabricated of a relatively stiff yet somewhat pliant material, which permits the device to be introduced into a patient's body (not shown) along a tortuous path. The delivery catheter 42 can be formed from plastic, metal, or composite materials, e.g., a plastic material having a wire, braid, or coil core, which may prevent kinking or buckling of the delivery catheter 42 during advancement. Examples of materials suitable for the delivery catheter 42 include, but are not limited to, polyimide, nylon, polyester, etc.

The delivery device 40 also includes an inflatable balloon or other expandable members 46 provided on the distal end 43 of the delivery catheter 42 for expanding and/or deploying the stent 41 placed on the balloon 46. The stent delivery device 40 also includes a stent deployment site locator 47 configured for locating an exact place for positioning the stent 41. The stent deployment site locator 47 can be either a dedicated separate device or a device integrated with the stent placement system 4.

According to the embodiment shown in FIG. 4A, the stent deployment site locator 47 is mounted on the delivery catheter 42 at the distal end 43, e.g., proximal or otherwise adjacent to the balloon 46. Generally, the stent deployment site locator 47 is constituted by a plurality of filament elements interconnected between a locator proximal end and a locator distal end; thereby forming a unitary structure.

According to the embodiment shown in FIG. 4A, the stent deployment site locator 47 includes wire loops which can be interlaced and or overlapped. The configuration and shape of the locator 47 in open condition is adapted for a proper positioning of the stent in an ostium (not shown). Various examples of the stent deployment site locator 47 will be shown hereinbelow.

When desired, the delivery device 40 may include one or more therapeutic and/or diagnostic elements (not shown) at the distal end 43 of the delivery catheter 42, e.g., instead of or in addition to the balloon 46 and/or stent 41.

The guiding catheter 48 of the stent placement system 4 can be in the form of a thin-walled, cylindrical flexible tube adapted to penetrate into a body passage (not shown) to reach the location where the stent should be placed. The delivery device 40 is mounted within the guiding catheter 48, and can be manipulated by the operator from the outside at the guiding catheter's proximal end (not shown).

The guiding catheter 48 may be constructed from substantially flexible, durable, strong and/or floppy materials. For example, the guiding catheter 48 can be made of a flexible, durable, strong plastic material and/or plastic having a braid or other reinforcement (not shown) that sufficiently supports the guiding catheter 48 to prevent kinking or buckling, while allowing the guiding catheter 48 to be directed easily through tortuous vessel ducts. Examples of the plastic include, but are not limited to, polyimide, polyvinyl chloride, nylon, teflon, etc. The guiding catheter 48 can also be made of a composite material, such as a wire mesh or a coil, (e.g., stainless steel coil). When desired, the guiding catheter 48 may be multi-layered with different materials in order to provide a graduated bending and stiffness characteristic over its length.

The guiding catheter 48 includes a lumen 49 for housing the stent delivery catheter 42. The lumen 49 has sufficient size for receiving the distal end 43 of the delivery catheter 42 therethrough together with the balloon 46 and the deployment site locator 47 in a contracted condition.

In operation, when the stent delivery device 40 moves within the guiding catheter 48, the stent deployment site locator 47 folds down to the dimension close to the inner diameter of the guiding catheter 48, and thus can easy slide along its inner surface. When the stent deployment site locator 47 is retracted from the guiding catheter 48 near an ostium, the deployment site locator opens, thereby restoring its original shape and taking a required position in a vascular tract. The stent deployment site locator 47 prevents the delivery catheter 42 to penetrate at the distance that is deeper than required, since it abuts a wall of the vessel at bifurcation point from which a lateral vessel departs.

When desired, the stent delivery device 40 may include a handle (not shown) on the proximal end to facilitate manipulating the delivery catheter 42. The handle can be integrated with a manipulator configured for manipulating the stent placement system 4 for delivering and placing the stent 41.

In addition, the stent delivery device 40 can include one or more inflation tubes 441 that extend from respective side inflation port(s) (not shown) in the handle through lumen of the delivery catheter 42 to openings (not shown in FIG. 4A) that communicate with an interior of a respective balloon 46. The balloon 46 can be inflated in order to expand the stent 41.

Furthermore, the stent delivery device 40 can include one or more guide wires 45 that extend from respective one or more guide wire port(s) at the proximal end (not shown) of the stent delivery device 40 through the lumen 44 of the delivery catheter 42 to an opening 461 arranged in a tip of the distal end 43 of the delivery catheter 42. The guide wire port(s) can be arranged in the delivery catheter 42, the guiding catheter 48 and/or in the handle, as will be described hereinbelow in detail.

Figure 4B:
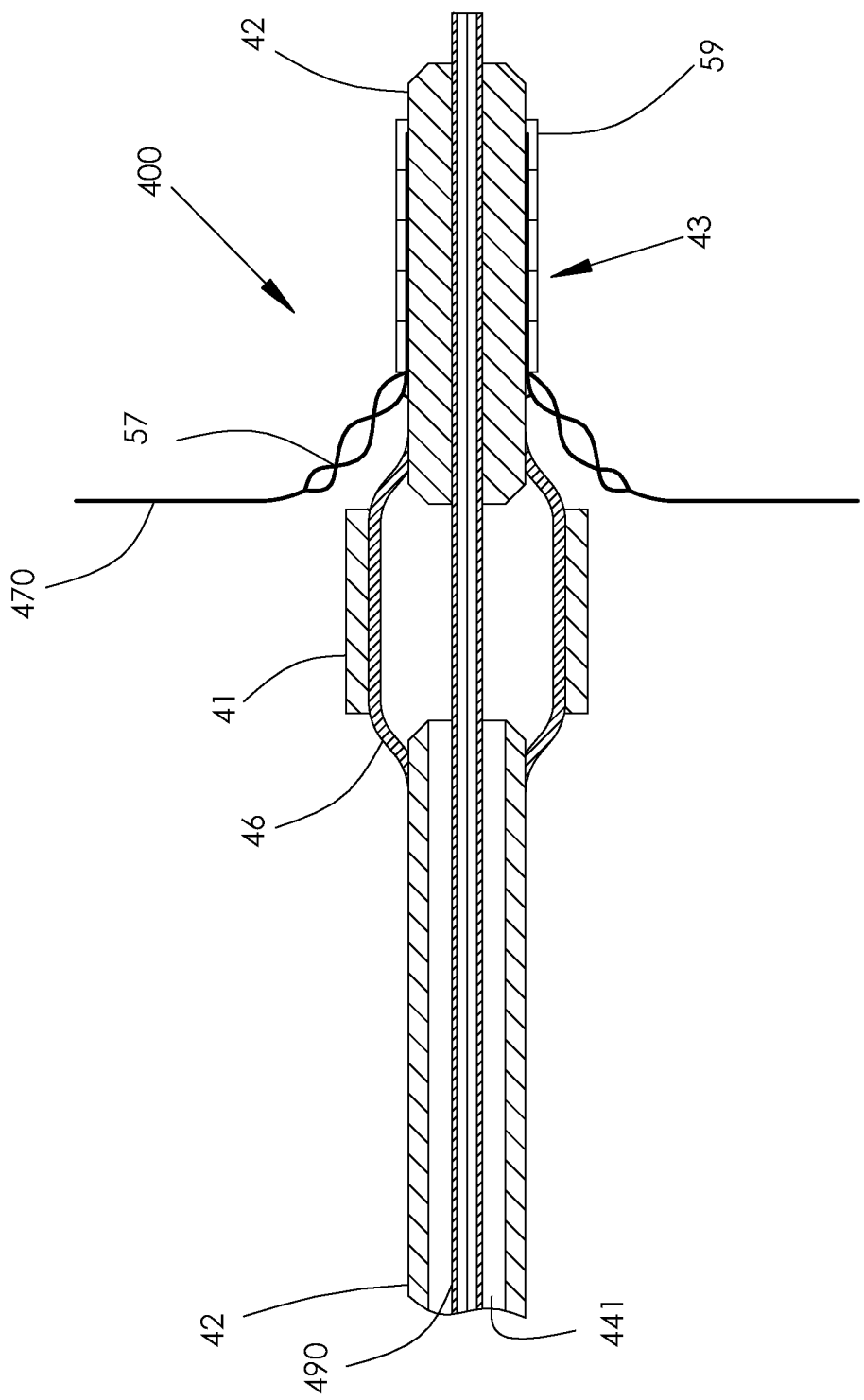
FIG. 4B illustrates a schematic longitudinal top cross-sectional fragmentary view of a distal portion of a stent placement system, according to another embodiment of the present invention.
Figure 4C:
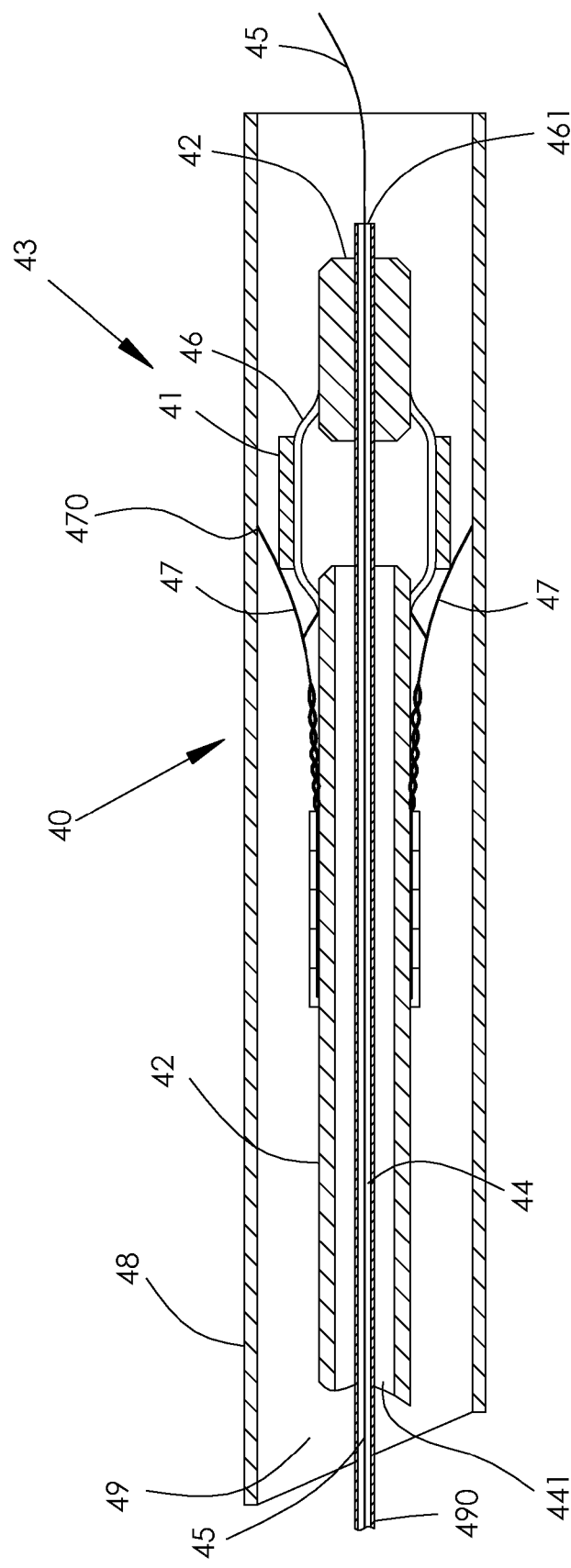
FIG. 4C illustrates a schematic longitudinal top cross-sectional fragmentary view of a distal portion of the stent placement system of the invention in which the stent delivery device is located within the guiding catheter.

FIG. 4C illustrates a schematic longitudinal top cross-sectional fragmentary view of a distal portion of the stent placement system of the invention in which the stent delivery device 40 is located within the guiding catheter 48. The stent deployment site locator 47 is folded down to the dimension close to the inner diameter of the guiding catheter 48, and can slide along its inner surface. In order to make the sliding of the locator 47 easy, a hydrophilic coating (not shown) can be applied to the external surface of distal end sections 470 of the locator 47. Examples of materials suitable for the hydrophilic coating of the locator 47 include, but are not limited to, polyarylene oxides, polyvinylpyrolidones, polyvinylalcohols, hydroxy alkyl cellulosics, algins, saccharides, caprolactones, and the like, and mixtures and combinations thereof. When desired, the stent deployment site locator 47 or at least the distal end sections 470 of the locator 47 can be coated with Teflon.

Figure 4D:
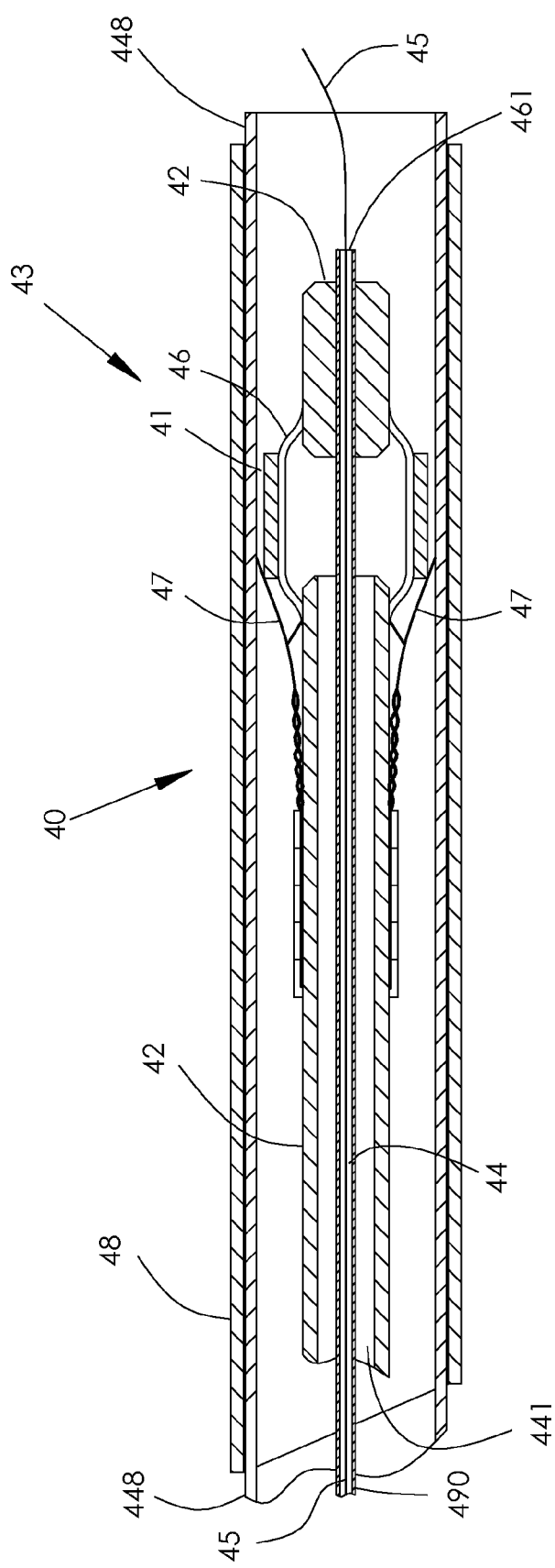
FIG. 4D illustrates a schematic longitudinal top cross-sectional fragmentary view of a distal portion of the stent placement system of the invention, in accordance with a further embodiment of the present invention.

Referring to FIG. 4D a schematic longitudinal top cross-sectional fragmentary view of a distal portion of the stent placement system of the invention is illustrated, in accordance with a further embodiment of the present invention. In this embodiment, in order to protect the inner surface of the guiding catheter 48 from scratches that can be caused by the locator 47 sliding within the guiding catheter 48, the stent placement system further includes a protective catheter 448. The protective catheter 448 operates as a sheath for the inner surface of the guiding catheter 48 to prevent from scratches.

In operation, when the locator 47 is retracted from the guiding catheter 48 together with the protective catheter 448, the protective catheter 448 can be removed leaving the inner surface of the guiding catheter 48 intact.

Referring to FIG. 4B, a schematic longitudinal top cross-sectional fragmentary view of a distal portion of a stent delivery device 400 is illustrated, in accordance with yet another embodiment of the present invention. The stent delivery device 400 differs from the stent delivery device 40 shown in FIG. 4A in the fact that the stent deployment site locator 470 is mounted after the balloon 46 in relation to a surgeon utilizing the delivery device.

Figure 9B:
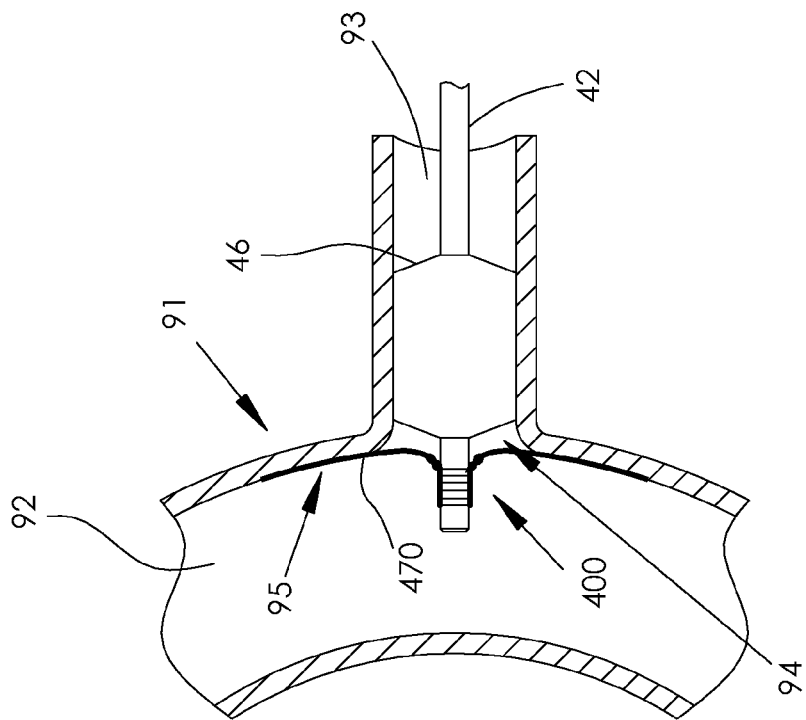
FIG. 9A and FIG. 9B illustrate cross-sectional fragmentary views of an organism and a method of utilizing of the stent delivery device shown in FIG. 4A and in FIG. 4B, respectively.
Figure 9A:
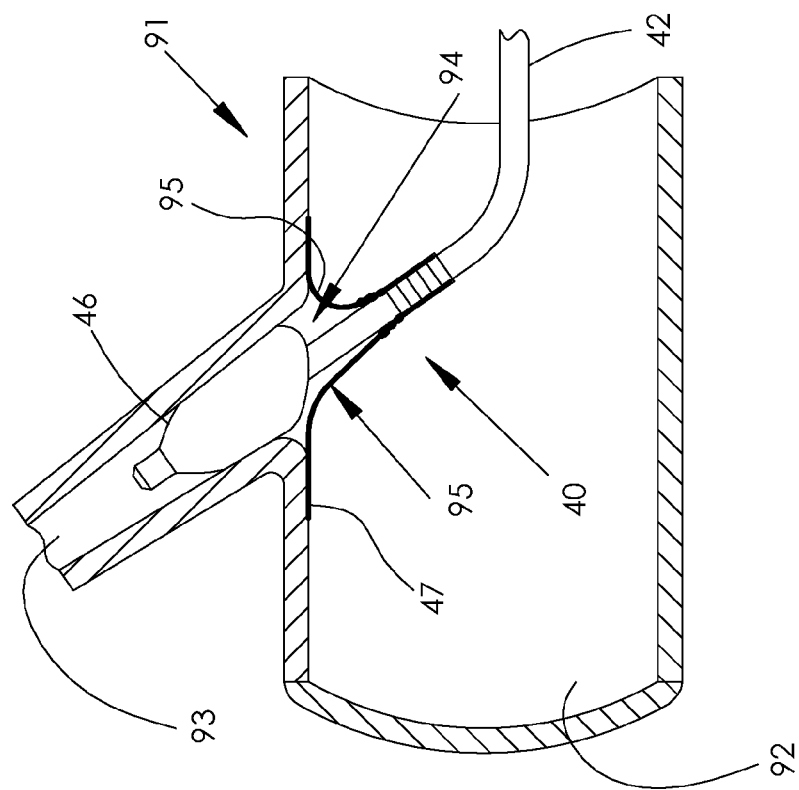

FIGS. 9A and 9B illustrate cross-sectional fragmentary views of an organism 91 and, the method of utilizing of the stent delivery device (40 in FIG. 4A) and the delivery device (400 in FIG. 4B), respectively. In particular, a fragment of the vascular or other tract of the organism 91 comprising a main trunk 92 that communicates with a branch trunk 93 is illustrated.

As shown in FIG. 9A, the stent delivery device 40 is inserted and advanced within the main trunk 92 towards the branch trunk 93 to the place where the intersection of the main trunk 92 with the branch trunk 93 forms an ostium 94 to be treated. A deployment site locator is positioned against an edge 95 of the ostium 94, whereas the balloon 46 is placed within the ostium 94 of the branch trunk 93.

In turn, as shown in FIG. 9B, the stent delivery device 400 is inserted and advanced within the branch trunk 93 to the place where the intersection of the main trunk 92 with the branch trunk 93 forms an ostium 94 to be treated. A deployment site locator 470 is positioned against an edge 95 of the ostium 94, whereas the balloon 46 is placed within the ostium 94 of the branch trunk 93.

While the stent deployment site locator (47 in FIG. 4A and 470 in FIG. 4B) has been described as being a component mounted on and integral with the delivery catheter 42, other configurations are also contemplated. In particular, the deployment site locator can be separate from, and moveable relative to, the delivery catheter 42.

Figure 10:
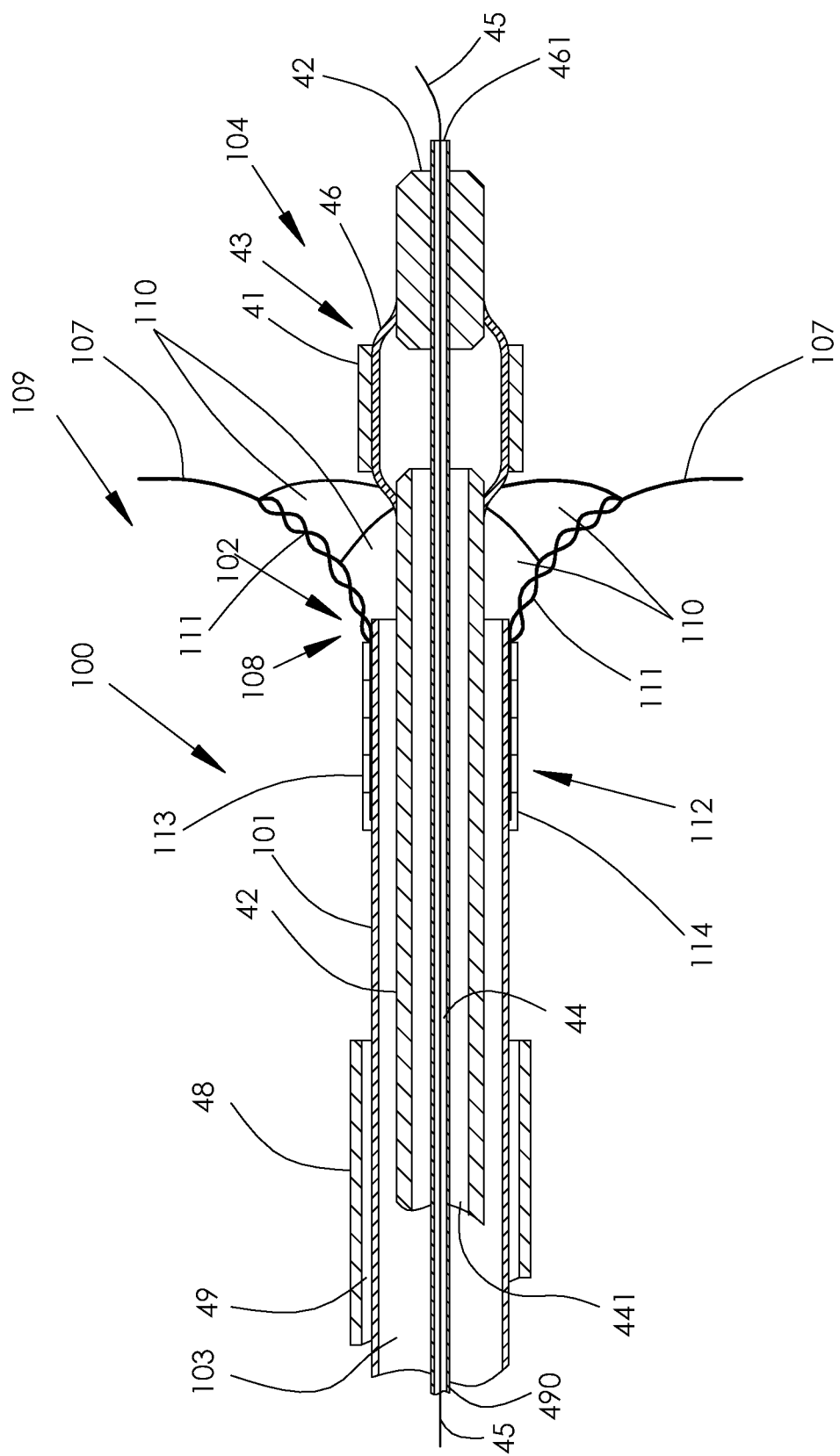
FIG. 10 illustrates a schematic longitudinal top cross-sectional fragmentary view of a distal portion of a stent placement system, according to yet another embodiment of the present invention.

Referring to FIG. 10, a schematic longitudinal top cross-sectional fragmentary view of a distal portion of a stent placement system 100 for delivering and placement of a stent 41 or other desired prosthesis into an ostium or other bifurcation of a vascular system or other tract of an organism (not shown) is illustrated, according to another embodiment of the present invention. The stent placement system 10 includes a stent delivery device 40, a guiding catheter 48 and a manipulator (not shown in FIG. 10) configured for manipulating the stent placement system 10 for delivering and placing the stent 41.

The stent placement system 10 includes a carrier catheter 101 formed as a tubular sleeve. The carrier catheter 101 has a proximal end (not shown), a distal end 102 and an axially extending inner lumen 103 provided within the carrier catheter 101 to permit a stent delivery device 104 to be inserted into the carrier catheter 101 from the proximal end. The outer diameter of the carrier catheter 101 should be less than the inner diameter of the guiding catheter 48 to permit the carrier catheter 101 to move within the guiding catheter 48.

The carrier catheter 101 can be a deflectable tube fabricated of a relatively stiff yet somewhat pliant material, which permits the device to be introduced into a patient's body (not shown) along a tortuous path. Examples of materials suitable for the carrier catheter 101 include, but are not limited to, polyimide, nylon, polyester, etc. When desired, the carrier catheter 101 may include a coil made from stainless steel, nitinol and/or other material. The carrier catheter 101 may be braided reinforced plastic catheters.

The stent delivery device 104 includes the delivery catheter 42 and the inflatable balloon 46 provided on the distal end 43 of the delivery catheter 42 for expanding and/or deploying the stent 41 placed on the balloon 46. Contrary to the stent delivery device (40 in FIG. 4A), the stent delivery device 104 does not include a deployment site locator. According to this embodiment, the stent deployment site locator 107 is formed at a distal portion of the tubular carrier catheter 101, either as an integral segment of the carrier catheter or as a separate device attached to the distal end of the carrier catheter 101 by means of a connector.

Generally, the stent deployment site locator 107 is constituted by a plurality of filament elements interconnected between a locator proximal end and a locator distal end; thereby forming a unitary structure.

According to one embodiment of the invention, the filament of the plurality of filament elements can extend from a locator proximal end 108 towards a locator distal end 109 and then return after winding to the proximal end 108 to form a plurality of filament loops 110. After forming the loops 110, the filaments are bound together in filament strands 111. The filament strands 111 are connected to the carrier catheter 101 along the surface circumference of a distal end 112 of the carrier catheter 101.

As shown in FIG. 10, the connection of the filament strands 111 to the tubular carrier catheter 101 is established by using a ferrule 113, such as a hollow cannula made of metal, e.g., stainless steel, etc.

Alternatively, a hollowed-out region (not shown) at the distal 112 end of the tubular carrier catheter 101 can be formed, and the filament strands 111 can be arranged in this hollowed-out region.

The filaments from the stent deployment site locator 107 can be coupled to the carrier catheter 101 along the surface circumference of the carrier catheter distal end 112 by one or more connecting means.

In one embodiment, the filament strands 111 can be connected to the carrier catheter 101 by using a suture, and/or wire or other known techniques. The connection can be carried out with or without glue and/or ferrule. When desired, the connection region may include a wire made of a radiopaque material.

Moreover, the filament strands 111 can be soldered, brazed or welded to the carrier catheter 101 at the joining portion, although other known techniques, such as gluing, may also be used. For instance, if soldering is used, the end of the carrier catheter 101 is first etched, preferably with acid, followed by neutralizing and drying. Flux is then applied to both the carrier catheter 101 and the cannula, the two are soldered together, and excess solder is removed. Afterwards, the parts should be neutralized, dried and cleaned. Likewise, a medically-acceptable adhesive may also be used to secure or join the filament strands 111 to the tubular carrier catheter 101. An example of the adhesive includes, but is not limited to, LOCTITE® 4011 cyanoacrylate.

In order to increase mechanical strength, when desired a thin tube (not shown) can be put on the filament strands 111 at the joining portion. The tube can be made of a thermo-shrinkable material, e.g., Polytetrafluoroethylene (PTFE), Polyester, or other material.

Figure 11:
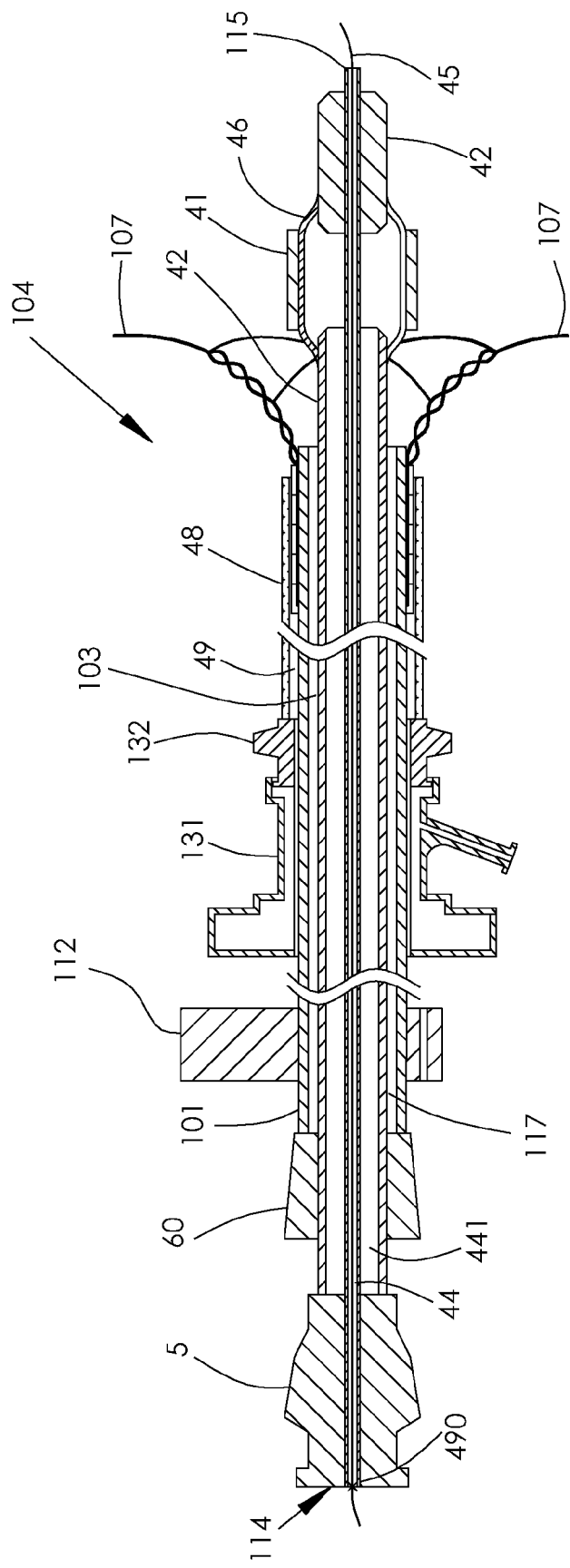
FIG. 11 illustrates a schematic longitudinal top cross-sectional fragmentary view of a stent placement system equipped with an Over-the-Wire delivery system according to one embodiment of the present invention.

Referring to FIG. 11, in order that the stent deployment site locator 107 mounted on the carrier catheter 101 be maintained at a desired location relative the balloon 46, according to an embodiment of the present invention, the stent placement system can include a clamp 112 arranged on the carrier catheter 101 for binding or pressing the carrier catheter 101 and the delivery catheter 42 together so as to hold them firmly and prevent their relative motion with respect to each other. It should be understood that the clamp 112 should not press over and close the internal lumens of the carrier catheter 101 which are intended for passing the delivery catheter 42 therethrough.

Moreover, according to an embodiment of the present invention, the stent placement system can further include a connector 131 for coupling the guiding catheter 48 to the carrier catheter 101 through a clip 132.

The stent delivery device 104 shown in FIG. 11 is usually referred to as an "Over-the-Wire" delivery system. According to this configuration, the guide wire 45 extends along the longitudinal axis of the delivery catheter 42 between a guide wire port arranged at the proximal end 114 of the delivery catheter 42 and the opening at the distal end 115. However, other configurations are also contemplated.

Figure 12A:
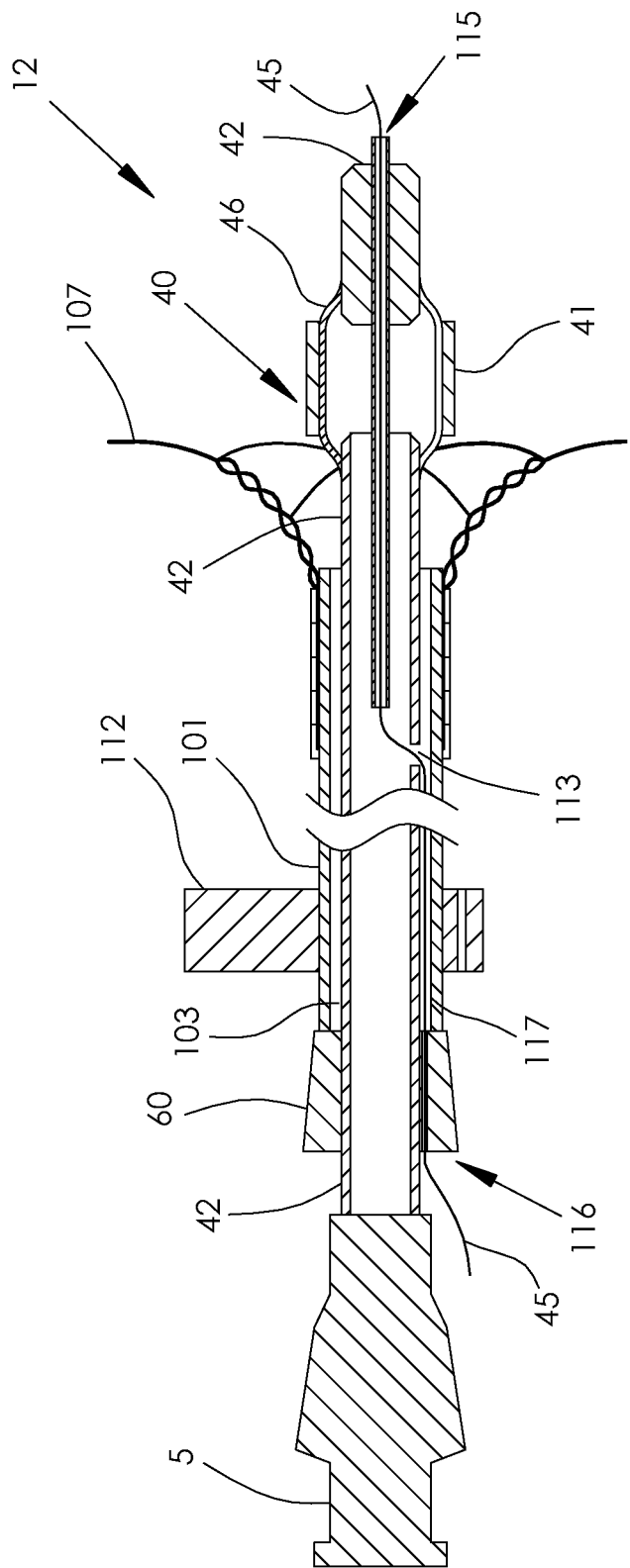
FIGS. 12A and 12B illustrate schematic longitudinal top cross-sectional fragmentary views of two embodiments of a stent placement system equipped with "Monorail" delivery systems.
Figure 12B:
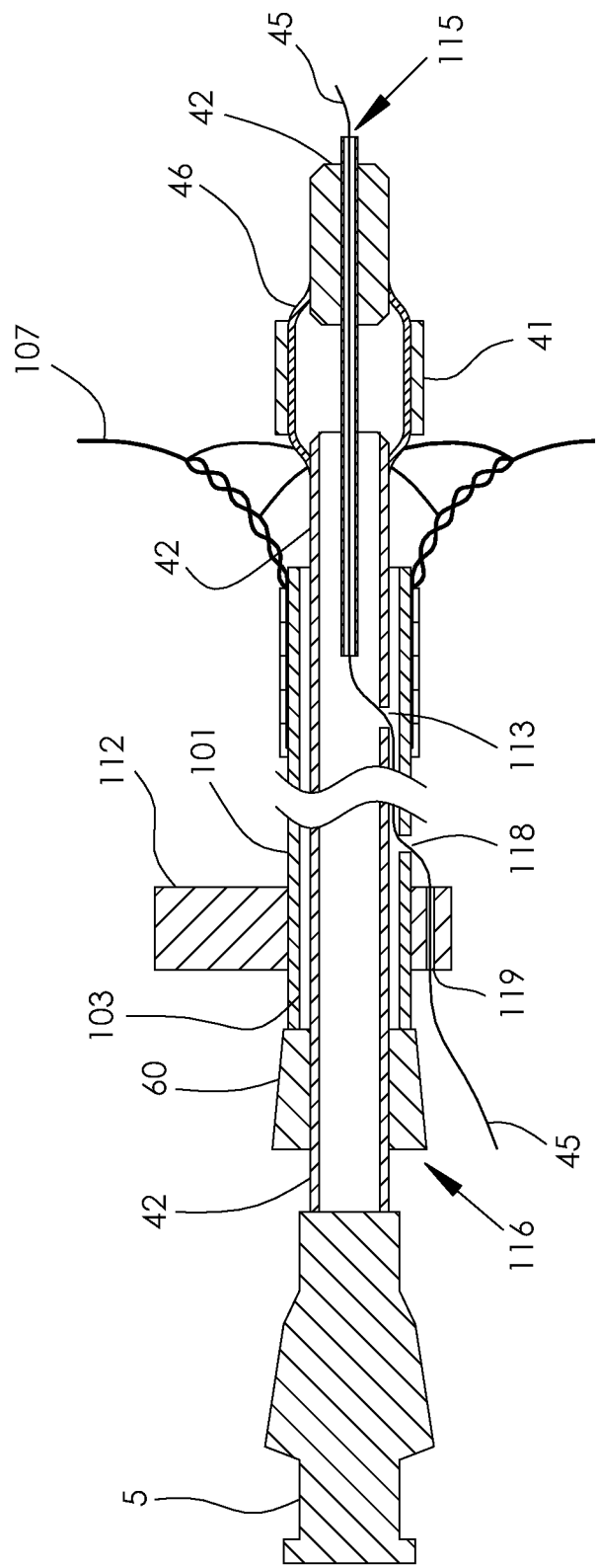

For example, FIGS. 12A and 12B illustrate two configurations that are usually referred to as "Monorail" delivery systems. The stent placement system 12 includes a stent delivery device 40, a carrier catheter 101 and a manipulator 5 configured for manipulating the stent placement system 12 for delivering and placing the stent 41.

As shown in FIG. 12A, the delivery catheter 42 may have a guide wire port (e.g., an opening) 113 arranged in the wall of the delivery catheter 42. The guide wire 45 extends between the distal end 115 and the opening 113 within the delivery catheter 42, passes through the opening 113, extends between the opening 113 and a proximal end 116 of the delivery catheter 42 within a gap 117 defined between the inner wall of the carrier catheter 101 and the outer wall of the delivery catheter 42. It should be understood that securing the guide wire 45 in the clamp 112, as shown above in FIG. 12A, transforms the "Monorail" delivery system into a "fixed wire" delivery system.

According to the embodiment shown in FIG. 12B, the carrier catheter 101 includes a guide wire port (e.g., an opening) 118. The guide wire 45 extends between the distal end 115 and the opening 113 within the delivery catheter 42, passes through the opening 113, extends between the opening 113 and the opening 118. Then, the guide wire 45 further passes through the opening 118 and extends to the clamp 112, where the guide wire 45 is secured in a clamp opening 119 to prevent movement relative to the carrier catheter 101 and the delivery catheter 42.

Figure 12C:
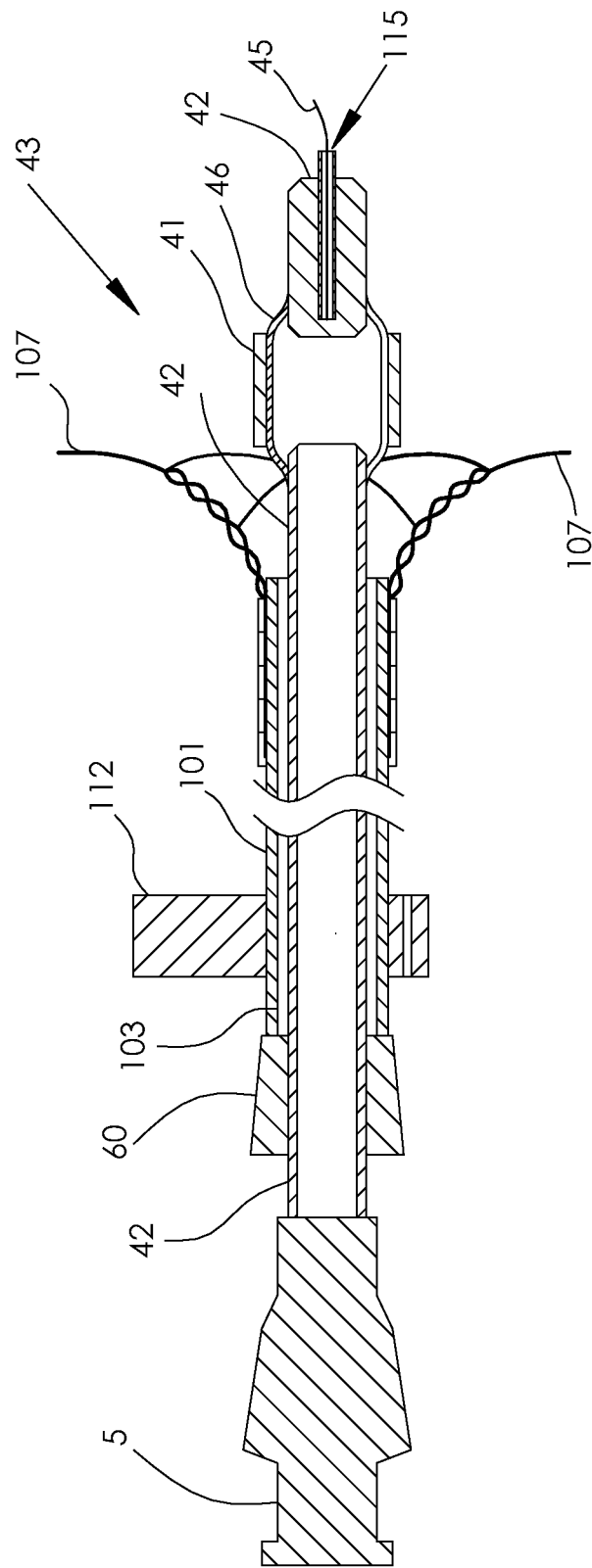
FIG. 12C illustrates a schematic longitudinal top cross-sectional fragmentary view of a stent placement system equipped with a "fixed wire" delivery system, according to one embodiment of the present invention.

Referring to FIG. 12C, the stent placement system is illustrated, according to yet another embodiment of the present invention. The configuration shown in FIG. 12C corresponds to a "fixed wire" delivery system that differs from the configurations shown in FIGS. 12A and 12B by the fact that the guide wire 45 is fixed at the distal end 43 of the delivery catheter 42.

Figure 13:
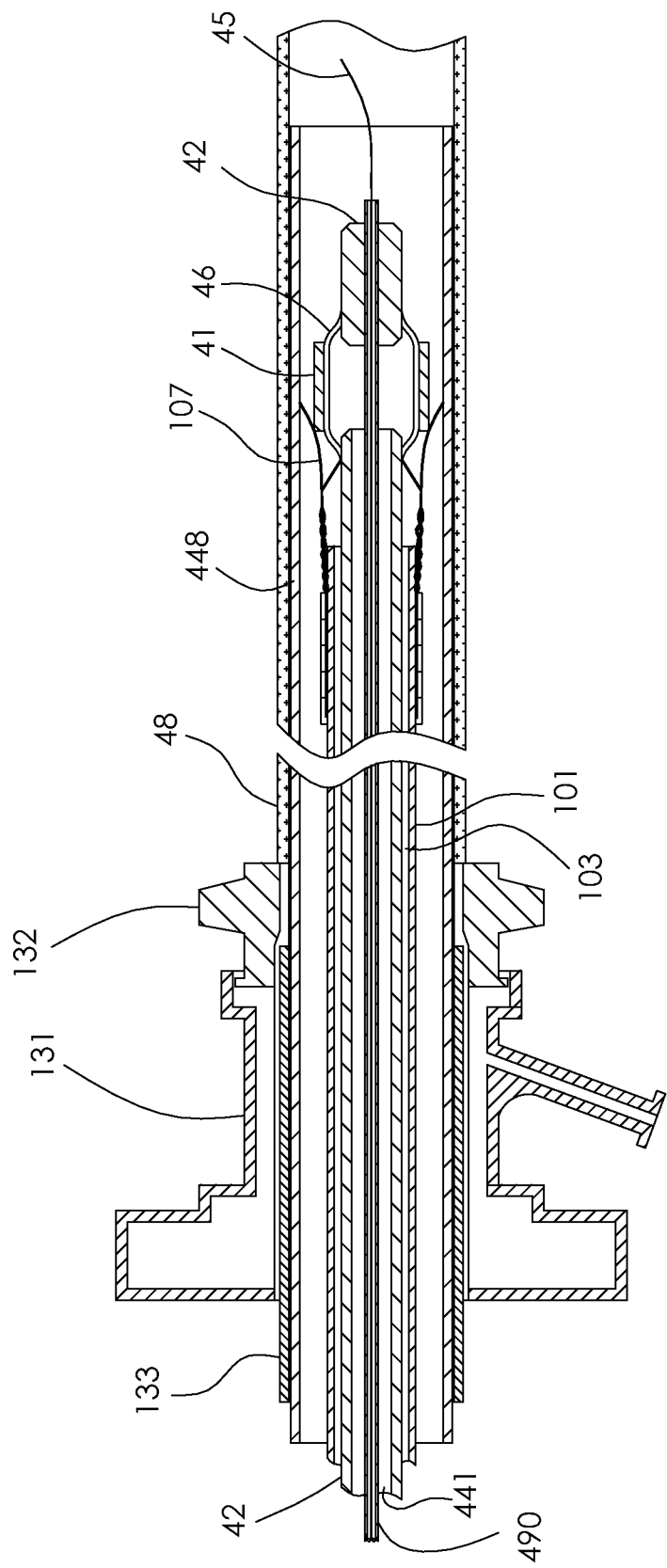
FIG. 13 illustrates the stent placement system, according to still another embodiment of the present invention.

Referring to FIG. 13, the stent placement system is illustrated, according to still another embodiment of the present invention. As shown in FIG. 13, the system includes most of the elements described above. In operation, the assembling of the stent placement system by an operator of the system begins from placing the guiding catheter 48 into a venous system or other tract of an organism. Thereafter, the guide wire 45 is introduced through the proximal end of the guiding catheter 48 to the desired location in the organism. The guide wire 45 can be used for introducing the delivery device including the delivery catheter 42 and the balloon 46.

The carrier catheter 101 can be introduced together with the protective catheter 448. Alternatively, the carrier catheter 101 can be introduced with an assistance catheter 133 that assists to fold the loops of the stent deployment site locator 107. The assistance catheter 133 can be introduced together with the carrier catheter 101 and the folded locator 107 into the connector 131 from the proximal end until the guiding catheter 48. Then, the carrier catheter 101 can be pushed towards the distal end, whereas the assistance catheter 133 can be removed from the stent placement system. An example of the assistance catheter 133 includes, but is not limited to, a peel-away sheath, which is known per se.

It should be understood that the assembling of the stent placement system described above is also applicable, mutatis mutandis, to the case when the stent deployment site locator is mounted on the delivery catheter (42 in FIG. 4A) at the distal end (43 in FIG. 4A).

A schematic longitudinal top cross-sectional fragmentary view of a stent delivery device 50 and a top view of an exemplary stent deployment site locator 51 of the delivery device 50 in a deployed (opened) position are illustrated in FIGS. 5A and 5B, respectively, according to one embodiment of the present invention. The structure of the stent deployment site locator 51 has a petal shape and comprises a proximal portion 52 and a distal portion 53, and is constituted by a plurality of filaments fabricated from one or more wires that extend from a locator proximal end 54 towards a locator distal end 55 and then return after winding to the proximal end 54 to form a plurality of filament loops 56. After forming the loops in the distal portion 53, the filaments are bound together in filament strands 57 at the proximal portion 53 of the deployment site locator 51.

Each filament originates from a certain point at the locator proximal end 54, and extends towards the locator distal end 55 to form a loop. After forming the loop, the filament returns to the same original point at the locator proximal end 54 to form one of the filament strands 57 in the proximal portion 52.

In the proximal portion 52, each side 59 of each loop 56 is directly connected to a side 59 of an adjacent loop 56 at one or more points along the proximal portion 52. Specifically, each side 59 of each loop 56 is connected to a side of an adjacent loop at continuous length sections, thereby forming a plurality of strands 57 at the locator proximal portion 52. This feature provides structural rigidity and dilatation ability to the locator. However, the loops 56 are not interconnected in the distal portion 53. Specifically, the loops 56 deploy radially outward and away from each other in the distal portion 53 when the locator is deployed outside the guiding catheter (not shown in FIGS. 12A-12C). This configuration maintains the loops in one plane, thereby providing a desired direction for the "balloon-stent pair".

According to one embodiment of the present invention, the connection of the sides 59 of the loops 56 in the proximal portion 52 is achieved by twisting each pair of the corresponding sides 59 by one or more turns and forming twisted parts of the strands 57. Likewise, the connection of the sides of the neighboring loops can also be achieved by soldering, brazing, gluing, etc.

The diameters of the filaments of the deployment site locator 51 may vary from wire-to-wire and/or along the lengths of each wire.

The filaments utilized for the fabrication of the deployment site locator 51 can be made of a suitable material that is suitably biocompatible and has thermo-mechanical shape memory and/or superelastic properties. According to one embodiment of the invention, the filaments are made of a metallic material. For example, the metallic material can be selected from a NiTi based alloy (e.g., Nitinol), stainless steel and other materials possessing good shape memory, elastic or superelastic characteristics. According to another embodiment of the invention, the filaments are made of non-metallic material, e.g. Capron, Nylon, etc.

According to a still further embodiment of the invention, the filaments of the deployment site locator are covered by an insulating layer. The insulating layer can, for example, be made of Teflon. The advantage of Teflon is its thermal resistance and low coefficient of mechanical friction, which leads to an additional reduction of traumatism.

Preferably, but not mandatory, the filaments are radiopaque, so as to permit them to be visualized by a fluoroscope with respect to the object to be retracted. Thus, according to one example, in order to provide radiopacity, the metallic material from which the filaments are made can include a material which provides radiopacity, e.g., a noble metal, such as gold, tantalum, platinum, etc. Likewise, the metallic material can be alloyed with one or more metals selected from Pd, W, Nb, Co, Cu, etc.

According to another example, the filaments are made of a core tube (cannular strand) containing an axially disposed radiopaque wire.

According to yet another example, the filaments can have radiopaque parts of a predetermined length. These radiopaque parts can form the distal portion of the deployment site locator 51 or at least a part of the distal portion.

Radiopacity can also be improved through coating processes such as sputtering or plating a radiopaque material onto the filaments, or the deployment site locator fabricated from these filaments, thereby to provide a radiopaque coating layer on the filaments.

Likewise, radiopacity can yet be improved by using radiopaque markers (not shown) which can be attached to or placed around the filaments forming the deployment site locator. In this manner, materials which have higher radiopacity than the deployment site locator structure itself, such as gold, tantalum or platinum, can be utilized as markers and be strategically placed along the body of the deployment site locator to increase the visualization of the deployment site locator. For example, the deployment site locator can comprise one or more radiopaque markers (not shown) attached to or placed around the filaments forming one or more filament loops 56 in the locator distal portion 53. For example, the radiopaque marker can be a ferrule put on the filament.

According to another embodiment of the invention, the filaments can be multi-wire strands. In such a case, in order to improve radiopacity, the multi-wire strands can include a central core wire and at least one another wire twisted about said central core wire which is made of a material having a level of radiopacity greater than the level of radiopacity of said central core wire. Examples of such a material include, but are not limited to, Pt, Au, Pd, Ta, etc.

According to one embodiment of the invention, the deployment site locator 51 is an integral part of the stent delivery device 50. In this case, at the locator proximal end 52, the filament strands 57 are directly connected to the delivery catheter 42 along the surface circumference at the delivery catheter distal end 43 before the balloon 46 in relation to a surgeon utilizing the delivery device 50. The filaments from the strands 57 can be trimmed and coupled to the delivery catheter 42 along the surface circumference by one or more connecting means.

In one embodiment, the filament strands 57 can be directly connected to the delivery catheter 42. For example, the filament strands 57 can be connected to the delivery catheter 42 by using a suture or a wire. The connection can be carried out with or without glue and/or ferrule. When desired, the connection region may include a wire made of a radiopaque material.

Moreover, the filament strands 57 may be soldered, brazed or welded to the delivery catheter 42 at the joining portion 58. Likewise, a medically-acceptable adhesive may also be used to secure or join the filament strands 57 to the delivery catheter 42. An example of the adhesive includes, but is not limited to, LOCTITE® 4011 cyanoacrylate.

In order to increase mechanical strength, a thin tube 59 can be put on the filament strands 57 at the joining portion 58, as shown in FIG. 5A. The tube 59 can be made of a thermo-shrinkable material. An example of the material suitable for the tube 59 includes but is not limited to Polytetrafluoroethylene (PTFE), Polyester, or other materials.

In another embodiment, a separate ferrule (not shown), can be used to connect the filament strands 57 or loops to the delivery catheter 42. The ferrule can be joined to the delivery catheter 42 and to the filament strands, preferably, by soldering, welding or brazing, although other known techniques, such as gluing, may also be used. For instance, if soldering is used, the end of delivery catheter 42 is first etched, preferably with acid, followed by neutralizing and drying. Flux is then applied to both the delivery catheter 42 and the cannula, the two are soldered together, and excess solder is removed. Afterwards, the parts should be neutralized, dried and cleaned.

Figure 4E:
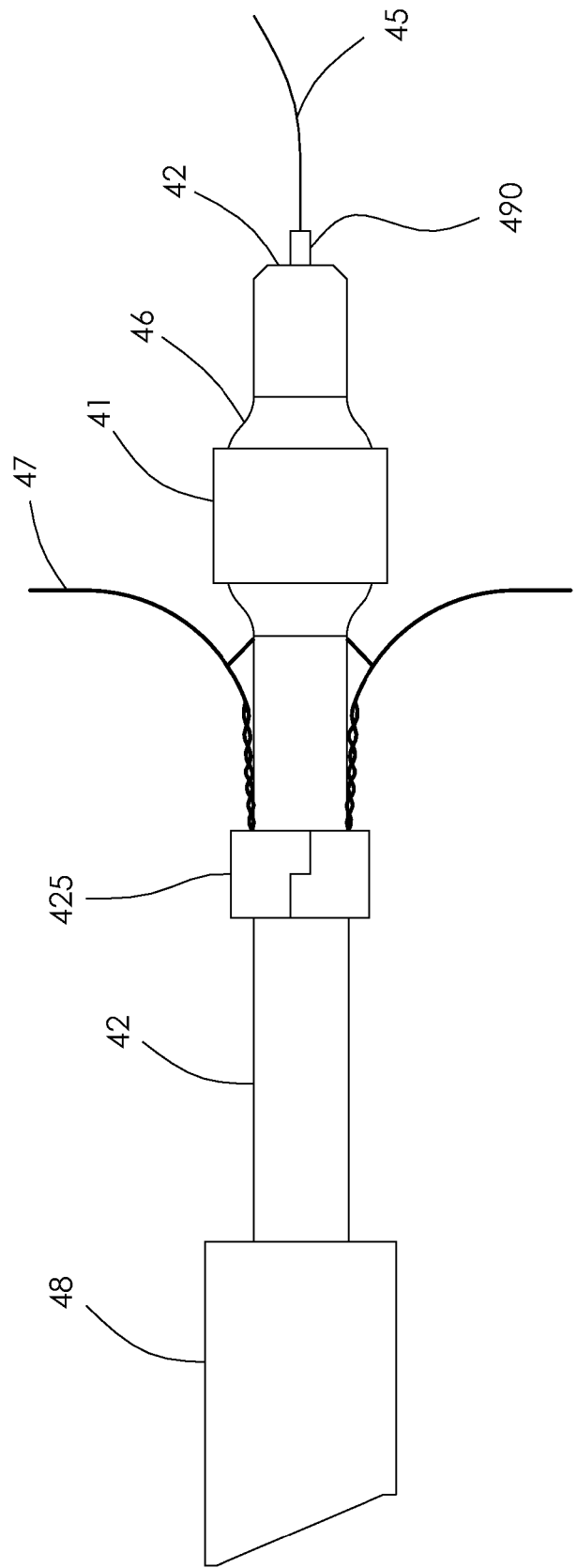
FIG. 4E shows a schematic longitudinal fragmentary view of a distal portion of a stent placement system in which the deployment site locator is coupled to the stent delivery device by means of a quick connector.

According to another embodiment of the invention, the deployment site locator can be a dedicated device fixed to the delivery catheter 42 by a special separate connector. FIG. 4E shows a schematic longitudinal fragmentary view of a distal portion of an exemplary stent placement system in which the deployment site locator 47 is coupled to delivery catheter 42 the stent delivery device by means of a quick connector 425. An example of the quick connector includes, but is not limited to, a bayonet lock connector. It should be understood that the quick connector can be installed to the locator and/or to the catheter by the methods described above.

Referring to FIG. 5C, a top view of an exemplary stent deployment site locator 501 of the delivery device (50 in FIG. 5A) in a deployed (opened) position is illustrated, according to another embodiment of the present invention. The locator 501 differs from the locator 51 shown in FIG. 5B in the fact that the distal end 55 of each of loop 56 is coupled to the distal end 55 of the neighboring loops 56 by means of a reinforcement wire 502 to provide mechanical strengthening to the stent deployment site locator 501. Such strengthening can be desired for avoiding the situations that may happen for the locator 51, when one uncoupled loop (petal) 56 can enter into an ostium, whereas all other petals remain outside of the ostium. Accordingly, the provision of the reinforcement wire 502 enables avoiding such situations. It should be understood that although coupling the distal end is a preferable embodiment, generally, the strengthening can be achieved by coupling any parts of distal portions of the neighboring loops.

Referring to FIGS. 6A and 6B together, an exemplary stent deployment site locator 61 is illustrated, according to another embodiment of the present invention. Similar to the structure shown in FIGS. 5A and 5B, the structure of the stent deployment site locator 61 comprises a locator proximal portion 62 and a locator distal portion 63, and is constituted by a plurality of filaments fabricated from one or more wires that extend from a locator proximal end 64 towards a locator distal end 65 and then return after winding to the proximal end 64 to form a plurality of filament loops 66. After forming the loops 66 in the locator distal portion 63, the filaments are bound together in filament strands 67 at the locator proximal portion 63 of the deployment site locator 61.

According to this embodiment, each filament extends from a certain point 610 at the locator proximal end 64, and then, after enwinding with other filaments, arrives at another point 611 at the locator proximal end 64, where the filaments meet with other filaments. In this case, each filament strand 67 is formed by two different filaments that correspond to the sides of adjacent loops. In the distal portion 63, the neighboring loops 66 are overlapped and/or interlaced at points 620 without binding the loops to each other in the points 620. This configuration of the loops defines a net at the locator distal portion.

The filaments of the deployment site locator 61 can be coupled to the delivery catheter 42 in a manner similar to that described above for coupling the filaments of the deployment site locator 51. The physical characteristics of the filaments of the deployment site locator 61 can be similar to that described above with respect to the deployment site locator 51.

Figure 6C:
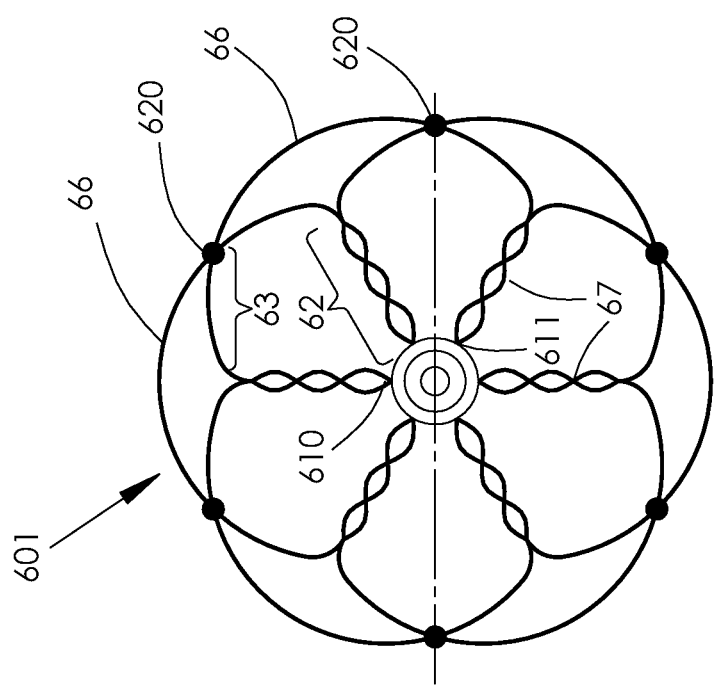
FIG. 6C illustrates a top view of a stent deployment site locator in a deployed position, according to a further embodiment of the present invention.

Referring to FIG. 6C, a top view of an exemplary stent deployment site locator 601 in a deployed (opened) position is illustrated, according to another embodiment of the present invention. The locator 601 differs from the locator 61 shown in FIG. 6B in the fact that the overlapped points 620 of the neighboring loops 66 are directly bound together to provide mechanical strengthening to the stent deployment site locator 601. The connection of the loops can, for example, be achieved by soldering, brazing, gluing, etc.

Figure 6D:
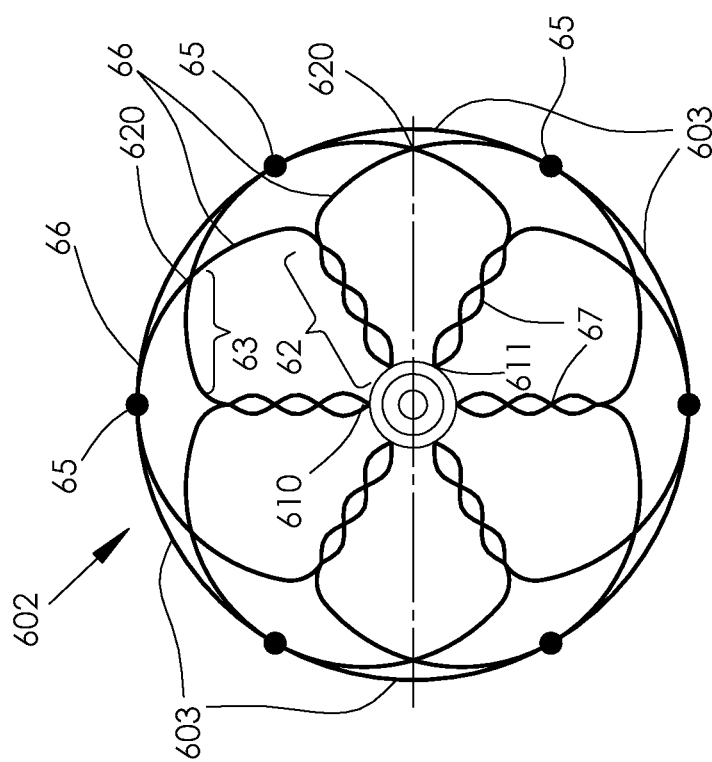
FIG. 6D illustrates a top view of a stent deployment site locator in a deployed position, according to still another embodiment of the present invention.

Referring to FIG. 6D, a top view of an exemplary stent deployment site locator 602 in a deployed (opened) position is illustrated, according to a further embodiment of the present invention. The locator 602 differs from the locator 61 shown in FIG. 6B in the fact that the distal end 65 of each of loop 66 is coupled to the distal end 65 of the neighboring loops 66 by means of a reinforcement wire 603 to provide mechanical strengthening to the stent deployment site locator 602.

When desired, the locator can have both features described above. Specifically, the overlapped points 620 of the neighboring loops 66 can be directly bound together; and the distal end 65 of each of loop 66 can be coupled to the distal end 65 of the neighboring loops 66 by means of a reinforcement wire 603 to provide mechanical strengthening to the stent deployment site locator.

Figure 6E:
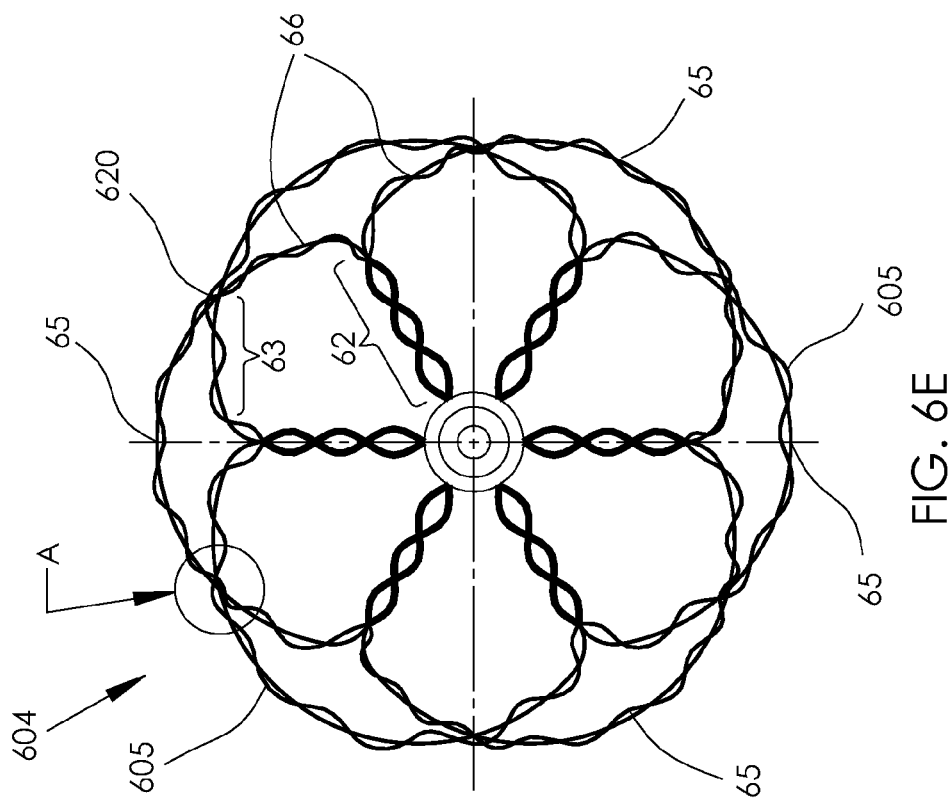
FIGS. 6E and 6F illustrate a top view of an exemplary stent deployment site locator in a deployed (opened) position, and amplified view of a selected portion in FIG. 6E, respectively, according to yet another embodiment of the present invention.
Figure 6F:
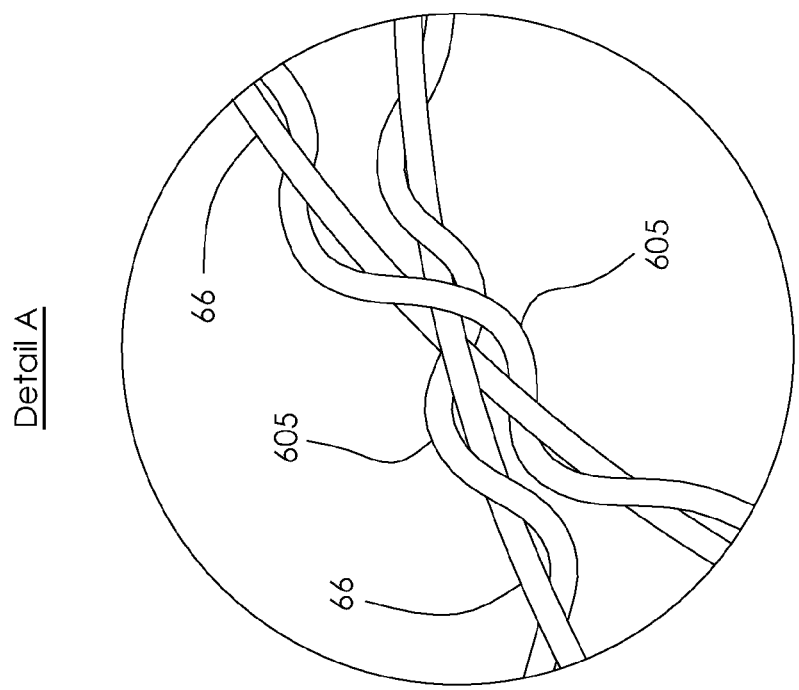

Referring to FIGS. 6E and 6F together, a top view of an exemplary stent deployment site locator 604 in a deployed (opened) position, and amplified view of a selected portion A are illustrated, respectively, according to yet another embodiment of the present invention. According to this embodiment, a mechanical strengthening of the locator 604 is achieved by providing one or more additional wires 605, and twisting these wires 605 around the loops 66 in the locator distal portion 63. The wires 605 can, for example, be made from the same material as the material of the loops 66. Alternatively, a different material having desired characteristics can be used, provided that the locator has sufficient strength and the loops are bound to each other.

Figures 7A, 7B:
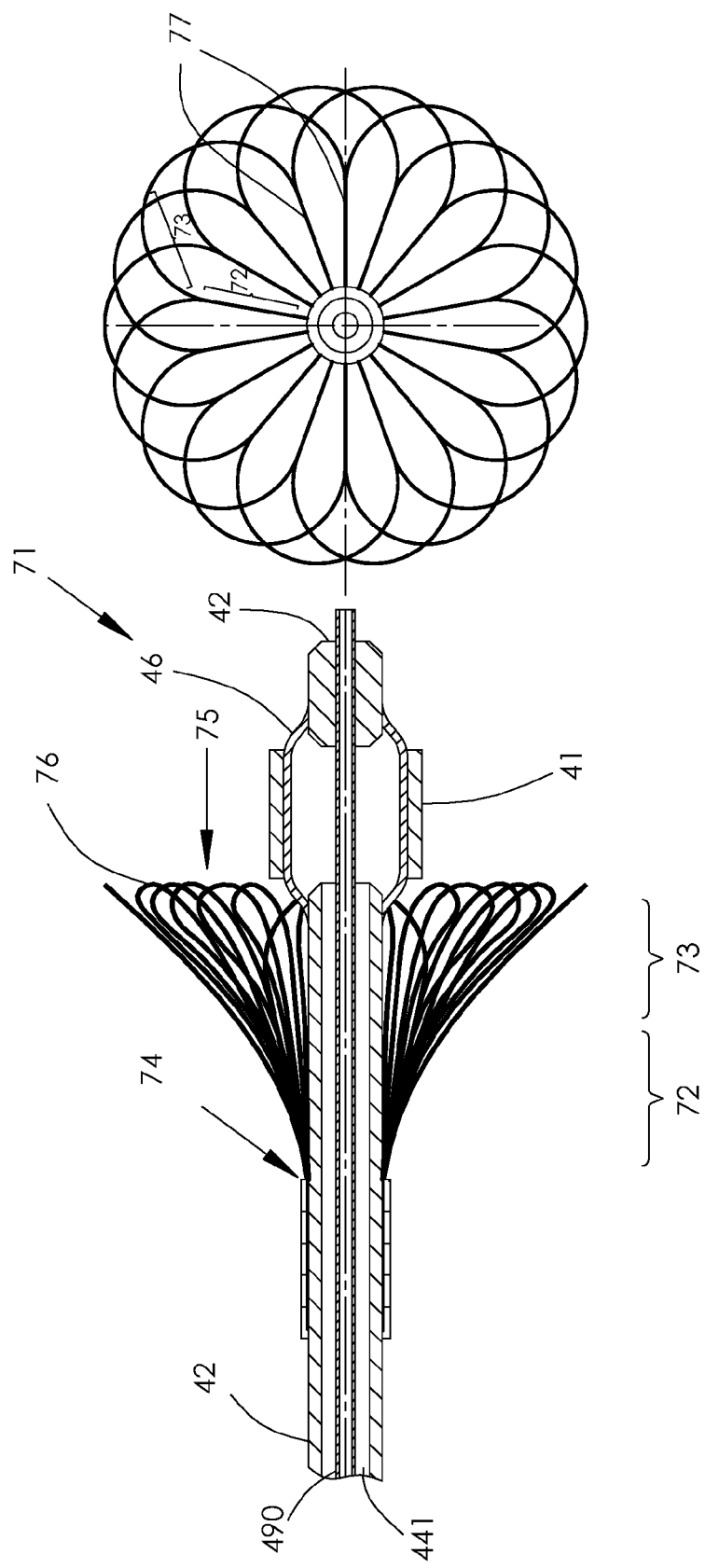
FIG. 7A and FIG. 7B illustrate side and top views of the distal portion of the stent delivery device equipped with a stent deployment site locator, according to a further embodiment of the present invention.

Referring to FIGS. 7A and 7B, an exemplary stent deployment site locator 71 is illustrated, according to a further embodiment of the present invention. The structure of the stent deployment site locator 71 comprises a proximal portion 72 and a distal portion 73, and is constituted by a plurality of filaments fabricated from one or more wires that extend from a locator proximal end 74 towards a locator distal end 75 and then return after winding to the proximal end 74 to form a plurality of filament loops 76. After forming the loops in the distal portion 73, the filaments are bound together in filament strands 77 at the proximal portion 73 of the deployment site locator 71.

The stent deployment site locator 71 differs from the stent deployment site locator 61 shown in FIGS. 6A and 6B by the fact that it includes more loops 76 and more strands 77. Accordingly, in the distal portion 73 each loop can be interlaced overlapped and/or interlaced with more than one other loop.

The physical characteristics of the filaments of the deployment site locator 71 can be similar to that described above with respect to the deployment site locator (51 in FIGS. 5A and 5B).

Referring to FIGS. 8A and 8B, an exemplary stent deployment site locator 81 is illustrated, according to a further embodiment of the present invention. The structure of the stent deployment site locator 81 is in the form of a basket, and is constituted by a plurality of filaments fabricated from one or more wires that extend from a locator proximal end 84 towards a locator distal end 85 and then return after winding to the proximal end 84 to form a plurality of filament loops 86 loops having various shapes and sizes. At least a part of the loops are overlapped and/or interlaced so as to define a net that imparts structural rigidity and dilatation abilities to the basket when opened.

The physical characteristics of the filaments of the deployment site locator 61 can be similar to that described above with respect to the deployment site locator (51 in FIGS. 5A and 5B).

From the foregoing description it should be appreciated that deployment site locators of the delivery system constructed in accordance with the present invention, can comprise a variety of user desired shapes, number of loops, shape of the loops, and types of connection of the loops in the proximal portion.

As such, those skilled in the art to which the present invention pertains, can appreciate that while the present invention has been described in terms of preferred embodiments, the concept upon which this disclosure is based may readily be utilized as a basis for the designing of other structures and processes for carrying out the several purposes of the present invention.

Although the present invention generally relates to improved stent placement, and the above embodiments describe use within an artery, the invention could be applied to any region of a person where a stent is to be deployed in a vessel. Moreover, it should be understood that the system of the present invention can also be used, mutatis mutandis, for delivering and placement of other desired medical devices into other bifurcation of tracts of an organism.

It should be understood that the medical device of the present invention is not limited to a medical treatment of a human body. It can be successfully employed for medical treatments of animals as well.

Also, it is to be understood that the phraseology and terminology employed herein are for the purpose of description and should not be regarded as limiting.

It is important, therefore, that the scope of the invention is not construed as being limited by the illustrative embodiments set forth herein. Other variations are possible within the scope of the present invention as defined in the appended claims. Other combinations and sub-combinations of features, functions, elements and/or properties may be claimed through amendment of the present claims or presentation of new claims in this or a related application. Such amended or new claims, whether they are directed to different combinations or directed to the same combinations, whether different, broader, narrower or equal in scope to the original claims, are also regarded as included within the subject matter of the present description.

The invention claimed is:

1. A system for delivering and placement of a medical prosthesis into an ostium of a tract system of an organism, comprising a stent delivery device including:
   a delivery catheter having a proximal end, a distal end, and at least one lumen extending between the proximal and distal ends;
   an inflatable balloon mounted on the distal end of the delivery catheter for expanding and deploying the medical prosthesis placed on the balloon; and
   a stent deployment site locator comprising a locator proximal portion and a locator distal portion, and constituted by a plurality of filament elements forming a flexible structure configured to be expanded into a deployed state for locating an exact place for positioning the medical prosthesis;
   wherein each said filament element extends from a locator proximal end towards a locator distal end and then returns after winding to the proximal end, thereby to form a plurality of filament loops, the loops being interconnected between the locator proximal end and the locator distal end to form a unitary structure;
   wherein each loop is connected to an adjacent loop at the locator proximal portion along a continuous length section of the loop to form a strand comprising said continuous length sections of two adjacent filament elements, and, when said locator proximal and distal portions are fully deployed, each loop is overlapped and/or interlaced with at least two neighboring loops at the locator distal portion, wherein the loops are directly bound together at overlapping points of the neighboring loops with formation of intermolecular interaction between the neighboring loops at the overlapping points, thereby providing mechanical strengthening to the stent deployment site locator; and
   wherein the loops deploy radially outward from each other at the locator distal portion.

2. The system of claim 1, wherein said stent deployment site locator is mounted on the delivery catheter at the distal end before the inflatable balloon in relation to an operator using the system.

3. The system of claim 1, wherein said stent deployment site locator is mounted on the delivery catheter at the distal end after the inflatable balloon in relation to an operator using the system.

4. The system of claim 1 comprising a carrier catheter configured for carrying said stent deployment site locator, wherein said carrier catheter has a proximal end, a distal end, and an axially extending inner lumen provided within the carrier catheter to permit the delivery catheter to be inserted into the carrier catheter from the proximal end; wherein said stent deployment site locator is mounted on the carrier catheter at the distal end.

5. The system of claim 4 comprising a clamp arranged on the carrier catheter for binding or pressing the carrier catheter and the delivery catheter together so as to hold them firmly and prevent their relative motion with respect to each other.

6. The system of claim 4 comprising a guiding catheter including a lumen for housing the carrier catheter, the lumen having sufficient size for receiving the distal end of the carrier catheter therethrough together with the stent deployment site locator in a contracted condition.

7. The system of claim 1 comprising a guiding catheter including a lumen for housing the delivery catheter, the lumen having sufficient size for receiving the distal end of the delivery catheter therethrough together with the stent deployment site locator in a contracted condition.

8. The system of claim 1 comprising a manipulator configured for manipulating the stent placement system for delivering and placing the medical prosthesis.

9. The system of claim 1 comprising a guide wire extending from a guide wire port at the proximal end of the stent delivery device through the lumen of the delivery catheter to an opening arranged in a tip of the distal end of the delivery catheter.

10. The system of claim 1, wherein the intermolecular interaction is created by one of: soldering, brazing, welding and gluing.

11. A deployment site locator for locating an exact place for positioning and facilitating the positioning of the medical prosthesis in or near an ostium, said deployment site locator having proximal and distal portions and comprising a plurality of filament elements forming an expandable flexible structure movable into a fully deployed state;
   wherein each said filament element extends from a locator proximal end towards a locator distal end and then returns after winding to the proximal end, thereby to form a plurality of filament loops, the loops being interconnected between the locator proximal end and a point spaced from the locator distal end to form a unitary structure;
   wherein each loop is connected to an adjacent loop at the locator proximal portion along a continuous length section of the loop, to form a strand comprising said continuous length sections of two adjacent filament elements, and, when said locator proximal and distal portions are fully deployed, each loop is overlapped and/or interlaced with at least two neighboring loops at the locator distal portion, wherein the loops are directly bound together at overlapping points of the neighboring loops with formation of intermolecular interaction between the neighboring loops at the overlapping points, thereby providing mechanical strengthening to the stent deployment site locator; and
   wherein the loops deploy radially outward from each other at the locator distal portion.

12. The deployment site locator of claim 11, wherein each filament of said plurality of filament elements originates from a certain point at the locator proximal end, and extends towards the locator distal end to form a loop and then returns to the same point at the locator proximal end.

13. The deployment site locator of claim 11, wherein said plurality of filament loops is not interconnected at said locator distal end.

14. The deployment site locator of claim 11, wherein a distal end of each loop is coupled to a distal end of the adjacent loops by means of a reinforcement wire connecting only distal ends of the loops to provide mechanical strengthening to the stent deployment site locator.

15. The deployment site locator of claim 11, wherein at least one wire is twisted around the loops at their distal portions to connect adjacent loops.

16. The deployment site locator of claim 11, wherein each side of each loop is directly connected to a side of an adjacent loop at more than one point, thereby to provide structural rigidity and dilatation ability to said deployment site locator.

17. The deployment site locator of claim 11, wherein the filaments of said plurality of filament elements are made of metallic material having superelastic and thermo-mechanical shape memory characteristics.

18. The deployment site locator of claim 17, wherein the metallic material includes a radiopaque material.

19. The deployment site locator of claim 11, wherein the filaments of said plurality of filament elements are made of non-metallic material.

20. The deployment site locator of claim 11 comprising a connector for coupling to a carrier catheter configured for carrying thereof.

21. The deployment site locator of claim 11, wherein the intermolecular interaction is created by one of: soldering, brazing, welding and gluing.

* * * * *